(12) United States Patent
Lunter et al.

(10) Patent No.: US 12,708,555 B2
(45) Date of Patent: Aug. 18, 2026

(54) APPARATUS FOR COLD AND HEAT THERAPY IN A RECLINED POSITION

(71) Applicant: JTL Enterprises, Inc., Clearwater, FL (US)

(72) Inventors: Paul Lunter, Palm Harbor, FL (US); Mario Simoes, Pinellas Park, FL (US); Timothy Elliot, Pinellas Park, FL (US); Kevin Conaway, Tampa, FL (US); Larry Johnson, Palm Harbor, FL (US); Jesse Palmer, Safety Harbor, FL (US)

(73) Assignee: JTL Enterprises, Inc., Clearwater, FL (US)

( * ) Notice: Subject to any disclaimer, the term of this patent is extended or adjusted under 35 U.S.C. 154(b) by 245 days.

(21) Appl. No.: 18/095,796

(22) Filed: Jan. 11, 2023

(65) Prior Publication Data

US 2023/0218429 A1 Jul. 13, 2023

Related U.S. Application Data

(60) Provisional application No. 63/299,326, filed on Jan. 13, 2022.

(51) Int. Cl.
*A61F 7/00* (2006.01)
*A61H 9/00* (2006.01)

(52) U.S. Cl.
CPC ......... *A61F 7/0053* (2013.01); *A61H 9/0021* (2013.01); *A61F 2007/0056* (2013.01); *A61H 2201/1654* (2013.01)

(58) Field of Classification Search
CPC ...... A61F 2007/0054; A61F 2007/0056; A61F 2007/0059; A61F 2007/0295;
(Continued)

(56) References Cited

U.S. PATENT DOCUMENTS 1,364,365 A 1/1921 Golden
1,790,364 A 1/1931 Bender et al.
(Continued)

FOREIGN PATENT DOCUMENTS

CN 304106145 4/2017
CN 110604418 A 12/2019
(Continued)

OTHER PUBLICATIONS

International Search Report and Written Opinion issued in PCT/US2023/010659, mailed Aug. 10, 2023, all enclosed pages cited.
(Continued)

*Primary Examiner* — Tigist S Demie
(74) *Attorney, Agent, or Firm* — Nelson Mullins Riley & Scarborough LLP

(57) ABSTRACT

An apparatus for cryotherapy treatment of a user in a reclined position, including a housing structure having a base portion with a user support surface for supporting the user in a reclined position, and a first fluid storage reservoir, a first fluid bag disposed within the user support surface, and a first fluid pump in fluid communication with both the first fluid storage reservoir and the first fluid bag, wherein the first pump is configured to circulate fluid from the first fluid storage reservoir to the first fluid bag.

20 Claims, 19 Drawing Sheets

(58) Field of Classification Search
CPC ...... A61F 2007/0296; A61F 2007/0298; A61F 7/0053; A61F 7/0085; A61H 2201/1654; A61H 9/0021; A61H 9/0078
See application file for complete search history.

(56) References Cited

U.S. PATENT DOCUMENTS

D209,643 S 12/1967 Mozneck
D217,449 S 5/1970 Meyer
3,826,250 A 7/1974 Adams
4,258,706 A 3/1981 Shank
4,281,224 A 7/1981 Castagna
4,565,188 A 1/1986 Hardie
4,635,620 A 1/1987 Ricchio
4,712,538 A 12/1987 Hardie et al.
4,976,256 A 12/1990 Marlin et al.
5,016,395 A 5/1991 Walker et al.
5,101,809 A 4/1992 Daffer et al.
5,380,269 A 1/1995 Urso
5,441,529 A 8/1995 Dorsch
5,503,618 A 4/1996 Rey
5,645,578 A 7/1997 Daffer et al.
5,725,472 A 3/1998 Weathers
6,036,663 A 3/2000 Arzt
6,272,697 B1 8/2001 Park
6,428,466 B1 8/2002 Licht et al.
6,497,717 B1 12/2002 Daffer et al.
6,572,570 B1 * 6/2003 Burns ................ A61H 33/6089 601/148
6,682,494 B1 1/2004 Sleichter, III et al.
D509,371 S 9/2005 Natuzzi
D530,933 S 10/2006 Vitaro
7,556,040 B2 7/2009 Meyer et al.
D602,269 S 10/2009 Jamison et al.
D608,555 S 1/2010 Aoki
8,348,871 B2 1/2013 Elliott et al.
D744,256 S 12/2015 Schoors et al.
D824,185 S 7/2018 Wang et al.
D840,183 S 2/2019 Rideau
D845,015 S 4/2019 Milne
D869,182 S 12/2019 Lin et al.
10,548,764 B2 2/2020 Alzeer et al.
10,561,250 B2 2/2020 Schwab
D889,864 S 7/2020 Bang et al.
D899,131 S 10/2020 Gray
D907,386 S 1/2021 Zheng et al.
D911,536 S 2/2021 Lunter et al.
D919,315 S 5/2021 Svendsen
D921,388 S 6/2021 Wang
D946,916 S 3/2022 Shin et al.
D951,668 S 5/2022 Li
D960,385 S 8/2022 Schubert et al.
D981,125 S 3/2023 Zhao
D992,293 S 7/2023 Seo
D1,035,895 S 7/2024 Lunter et al.
2001/0051565 A1 12/2001 Alessandri
2002/0151830 A1 10/2002 Kahn
2003/0013969 A1 1/2003 Erikson et al.
2003/0089370 A1 5/2003 Daffer et al.
2003/0139693 A1 7/2003 Swift
2004/0260364 A1 12/2004 Daffer et al.
2005/0059910 A1 3/2005 Licht et al.
2005/0203447 A1 9/2005 Pisani et al.
2006/0129074 A1 6/2006 Wang
2007/0100261 A1 5/2007 Turell et al.
2007/0256607 A1 11/2007 Friedman
2008/0097259 A1 4/2008 Flick et al.
2008/0235872 A1 10/2008 Newkirk et al.
2009/0019634 A1 1/2009 Lipponen
2009/0031267 A1 1/2009 Ueki
2009/0222070 A1 9/2009 Daffer
2009/0312679 A1 12/2009 Elliott et al.
2009/0312680 A1 12/2009 Lunter et al.
2010/0191158 A1 7/2010 Leventhal et al.
2010/0204760 A1 8/2010 Lawliss
2010/0286752 A1 11/2010 Hirata
2011/0030141 A1 2/2011 Soderberg et al.
2011/0251535 A1 10/2011 Bender
2012/0016274 A1 1/2012 Howe
2013/0096473 A1 4/2013 Berezhov
2014/0222121 A1 * 8/2014 Spence .................... A61F 7/02 607/104
2016/0008568 A1 1/2016 Attia et al.
2016/0029808 A1 2/2016 Youngblood et al.
2016/0081877 A1 3/2016 Marconi et al.
2016/0127129 A1 5/2016 Chee et al.
2016/0140307 A1 5/2016 Brosnan et al.
2016/0206506 A1 7/2016 Henkemans
2017/0143565 A1 5/2017 Childs et al.
2018/0160819 A1 6/2018 Rutledge
2018/0360649 A1 12/2018 Daffer
2019/0262169 A1 8/2019 Vergara et al.
2020/0027607 A1 1/2020 Muller
2020/0115200 A1 4/2020 Sellman et al.
2020/0139870 A1 5/2020 Mergl et al.
2020/0170882 A1 * 6/2020 Park .................... A61H 9/0078
2020/0276076 A1 9/2020 Lunter et al.
2021/0007928 A1 * 1/2021 Howe ................ A61H 15/0078
2021/0022564 A1 1/2021 Yoo et al.
2022/0071402 A1 3/2022 Pallett
2022/0125674 A1 4/2022 Lunter et al.
2023/0144593 A1 5/2023 Howe
2023/0218429 A1 7/2023 Lunter et al.
2024/0252385 A1 8/2024 Lunter et al.

FOREIGN PATENT DOCUMENTS

CN 110624180 A 12/2019
CN 110680729 A 1/2020
CN 110881880 A 3/2020
DE 19716808 A1 10/1998
KR 101393283 B1 5/2014
TW 201028139 A 8/2010
TW M469905 U 1/2014
WO 2022/094006 A1 5/2022
WO 2023/137092 A2 7/2023

OTHER PUBLICATIONS

International Preliminary Report on Patentability issued in PCT/US2023/010659, mailed Jul. 25, 2024, all enclosed pages cited.

CryoLounge Logo, wellnessspace.com, [online], [site visited Aug. 25, 2023], Available from internet URL: https://wellnessspace.com/cryolounge-plus/ (Year: 2023).

Cryo Lounge AR, first available Aug. 17, 2023, facebook.com, [online], [site visited Aug. 25, 2023], Available from internet URL: https://business.facebook.com/permalink.php?story_fbid=pfbid031UQBGJACDhmBb1JZQyTtoBGNk2LsFXreNy7w8HF6ejcjDXoLPSkyT8KAXBqSxP6MI&id=100094028918929 (Year: 2023).

International Search Report and Written Opinion, PCT/US 21/56930, dated Febuary 25, 2022, 11 pages.

Dry Heat Pods, Wellness USA, [Post date Jan. 24, 2022], [Site seen Jul. 10, 2023], Seen at URL: < https://wellness-USA.com/copy-3/> (Year: 2022).

RelaxSpace Wellness pod, Relax, [Post date: Jun. 25, 2022], [Site seen Jul. 10, 2023], seen at URL: https://wellnessspace.com/ relaxspace-wellness-pods/ (Year: 2022).

Extended European Search Report in European National Phase Patent Application No. 21887476.6, issued Aug. 9, 2024, all enclosed pages cited.

Taiwanese Office Action in Taiwanese Patent Application No. 110140164, issued Dec. 23, 2024, all enclosed pages cited.

Partial European Search Report in European National Phase Patent Application No. 23740646.7, issued Dec. 11, 2025, all enclosed pages cited.

Supplemental Extended European Search Report and Opinion in European Patent Application No. 23740646.7, issued Apr. 23, 2026, all enclosed pages cited.

* cited by examiner 200
206
218
202

200
206
218
202

200
202

200
218
202
206

200
206
218
202
204

210
210
210
210
202
200
206
210
218

APPARATUS FOR COLD AND HEAT THERAPY IN A RECLINED POSITION

CLAIM OF PRIORITY

This application claims priority to U.S. provisional patent application No. 63/299,326, filed on Jan. 13, 2022, the disclosure of which is incorporated by reference herein.

FIELD OF INVENTION

The present disclosure relates generally to apparatus for applying therapeutic treatments to the body of a user and, more particularly, to an apparatus utilizing cold and hot temperatures on a user during cryotherapy treatments.

BACKGROUND

Cryotherapy treatments utilizing extremely cold temperature fluids have gained popularity in recent years to help users with pain relief, muscle recovery, prevention of inflammation, etc. However, various issues and potential dangers exist for known methods of applying cryotherapy treatments. For example, direct contact with the extremely cold fluids, or containers they are enclosed within, may lead to hypothermia, skin irritation, and even frost bite in extreme circumstances. As well, existing treatments often require highly trained personnel to administer them which leads to reduced availability and increased expense. Moreover, existing treatments often require direct contact with the liquids, such as submersion in ice baths, which require the person undergoing the treatments to achieve some level of undress which may lead to inconvenience. Lastly, some methods of application include the utilization of ice and heat packs that can be rather inconvenient.

As well, massage is a time-honored and effective therapy for achieving relaxation, as well as treating muscular injuries, strains and general soreness. However, although massage is recommended by many physicians for such purposes, similarly to traditional cryotherapy treatments, massage therapy often has limited availability due to a scarcity of trained, qualified masseurs. As a result, many devices and apparatus have been proposed in the past for producing a massage-like manipulation of a user's body by various means, ranging from mechanically or electrically generated vibrations or pulsations, often accompanied by heating.

The majority of such known massage apparatus are in the form of a bed-type structure having an essentially horizontal user support surface on which the user may lay in a recumbent position. Advantageously, the horizontally recumbent position of the user's body in such bed-type structures enables either a portion or the entire length of the user's body to be treated by the massage apparatus. On the other hand, one of the disadvantages of a bed-type massage apparatus is that the supine disposition of the user is not conducive to enabling the user to engage in other activities during the operation of the apparatus, e.g., reading, watching television, operation of a laptop computer or other personal electronic device, etc. Additionally, experience has shown that many individuals feel uncomfortable using an open bed-type massage apparatus in public in which they are required to lie down on the machine and visible to all other occupants of the room in which the massage apparatus is disposed. Many users suggest that a reclined or seated disposition would lead them to feel less vulnerable, as well as an apparatus that offered more privacy than a standard bed-type apparatus. As well, because the known bed-type massage apparatus have no structure above the flat bed-type structure, the user is subjected to the environment (gym, care facility, etc.) surrounding the massage apparatus, which may lack the proper ambiance to achieve the desired level of relaxation. For such reasons, a desire has been expressed in the industry for a dry hydro-therapy massage apparatus wherein the user rests in a generally seated disposition during operation of the apparatus, allowing the user to read a book or magazine, watch television, or remain otherwise occupied with other activities.

As such, there exists a need for cold and hot therapy apparatus that facilitate the applications of treatments to a user while overcoming and/or reducing some of the above noted obstacles to treatment.

SUMMARY

One embodiment in accordance with the present disclosure is an apparatus for cryotherapy treatment of a user in a reclined position, including a housing structure having a base portion with a user support surface for supporting the user in a reclined position, and a first fluid storage reservoir, a first fluid bag disposed within the user support surface, and a first fluid pump in fluid communication with both the first fluid storage reservoir and the first fluid bag, wherein the first pump is configured to circulate fluid from the first fluid storage reservoir to the first fluid bag.

Yet another embodiment of the present disclosure is an apparatus for treatment of a user, having a housing structure including a base portion with a user support surface for supporting the user in a reclined position, and a top cover structure extending the length of the base portion, and a massage assembly disposed adjacent the user support surface, the massage assembly having a fluid spray assembly disposed within the base portion of the housing structure for directing a fluid stream at the user support surface for imparting a massaging effect through the user support surface to an upper body portion and a lower body portion of the user.

The accompanying drawings, which are incorporated in and constitute a part of this specification, illustrate one or more embodiments of the disclosure and, together with the description, serve to explain the principles of the invention.

BRIEF DESCRIPTION OF THE DRAWINGS

A full and enabling disclosure of the present disclosure, including the best mode thereof, directed to one of ordinary skill in the art, is set forth in the specification, which makes reference to the appended drawings, in which.

Figure 1A:
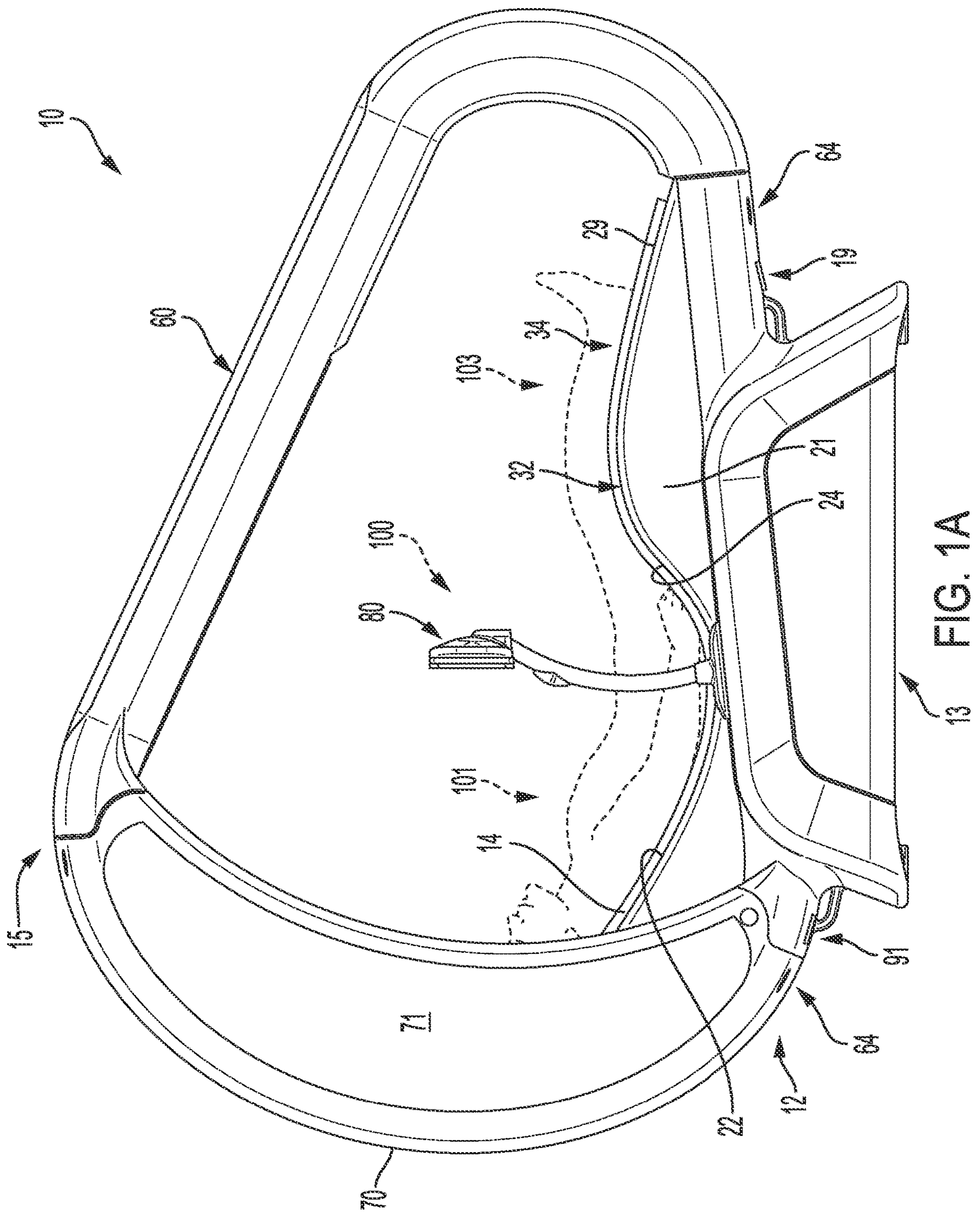
FIGS. 1A, 1B, and 1C are a right-side plan view, a front perspective view, and a rear perspective view of a recovery and wellness pod apparatus in accordance with an embodiment of the present disclosure.

Repeat use of reference characters in the present specification and drawings is intended to represent same or analogous features or elements of the invention according to the disclosure.

DETAILED DESCRIPTION

Reference will now be made in detail to presently preferred embodiments of the invention, one or more examples of which are illustrated in the accompanying drawings. Each example is provided by way of explanation, not limitation, of the invention. In fact, it will be apparent to those skilled in the art that modifications and variations can be made in the present invention without departing from the scope and spirit thereof. For instance, features illustrated or described as part of one embodiment may be used on another embodiment to yield a still further embodiment. Thus, it is intended that the present invention covers such modifications and variations as come within the scope of the appended claims and their equivalents.

Figure 1B:
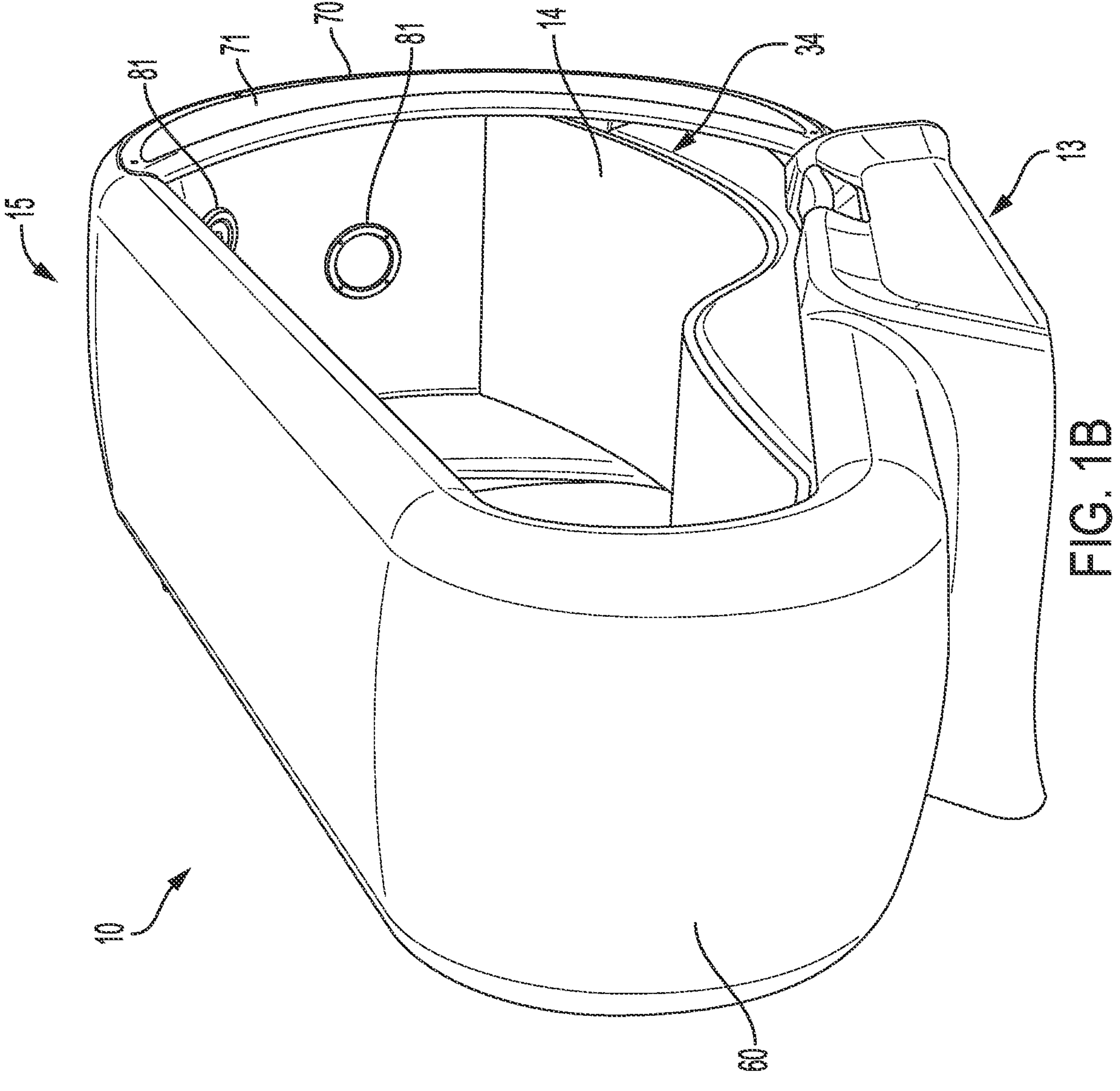
Figure 1C:
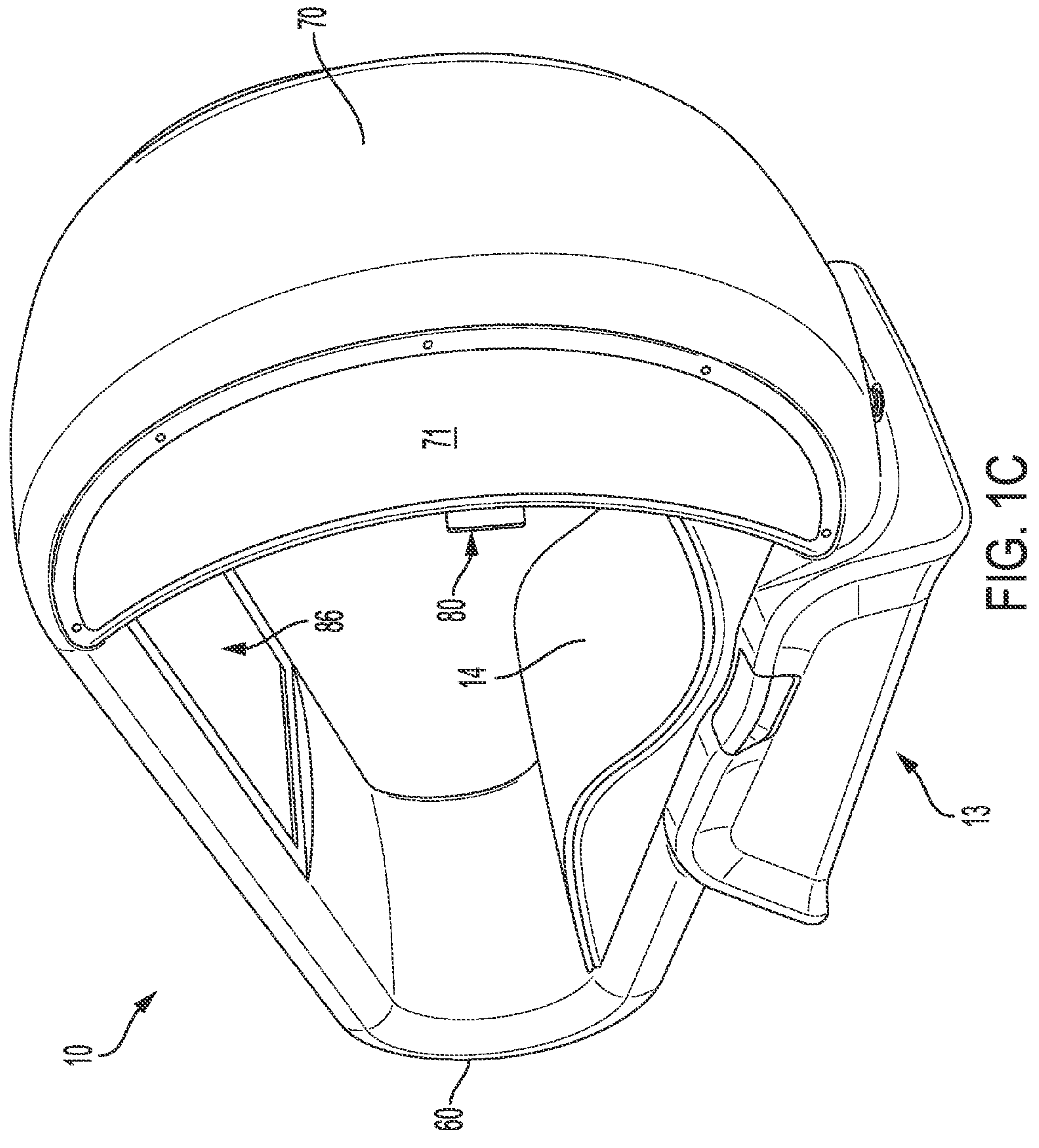

As used herein, terms referring to a direction or a position relative to the orientation of the recovery and wellness pod assembly, such as but not limited to "vertical," "horizontal," "top," "bottom," "above," or "below," refer to directions and relative positions with respect to the recovery and wellness pod assembly's orientation in its normal intended operation, as indicated in FIGS. 1A, 1B, and 1C. Thus, for instance, the terms "vertical" and "top" refer to the vertical orientation and relative upper position in the perspective of FIGS. 1A, 1B, and 1C and should be understood in that context, even with respect to a recovery and wellness pod assembly that may be disposed in a different orientation.

Further, the term "or" as used in this application and the appended claims is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "and" as used in this application and the appended claims should generally be construed to mean "one or more" unless specified otherwise or clear from the context to be directed to a singular form. Throughout the specification and claims, the following terms take at least the meanings explicitly associated herein, unless the context dictates otherwise. The meanings identified below do not necessarily limit the terms, but merely provide illustrative examples for the terms. The meaning of "a," "and," and "the" may include plural references, and the meaning of "in" may include "in" and "on." The phrase "in one embodiment," as used herein, does not necessarily refer to the same embodiment, although it may.

As will be readily understood by persons skilled in the relevant art, the recovery and wellness pod apparatus of the present disclosure is readily adapted to be embodied in many and various forms to accommodate relaxation of a user in differing reclined positions. The present disclosure is described herein in one contemplated embodiment of such apparatus, but only for purposes of providing an exemplary enabling disclosure of the invention and, in particular, the invention is not intended to be limited, and should not be construed as limited, to application or embodiment in such apparatus nor any other particular structure except as defined in the claims appended hereto.

Referring now to the accompanying drawings and initially to FIGS. 1A through 1C, a recovery and wellness pod apparatus according to one embodiment of the present disclosure is generally indicated at 10. The pod apparatus 10 includes a housing structure, generally indicated at 12, generally in the form of a hollow lounge chair-style base housing shell 13, including a top cover structure 15 extending the length thereof. The base housing shell 13 presents an upwardly facing top side configured to receive a user support surface 34 thereon that is designed for a user 100 to rest thereon for treatment. These treatments may include, but not limited to, massage, aromatherapy, auditory sessions, etc., in a seated reclining position, as more fully explained hereinafter. A fluid spray assembly, generally indicated at 16 (FIG. 4), is disposed within the base housing shell 13 in association with a pressurized fluid supply arrangement 18, which is disposed within the hollow base housing shell as well and includes a pump 28, preferably a liquid pump, for directing a pressurized fluid emission from a liquid storage reservoir 29 at the underside of the user support surface 34 to transmit a massaging effect therethrough to the body of the user 100 seated thereon.

Figure 4:
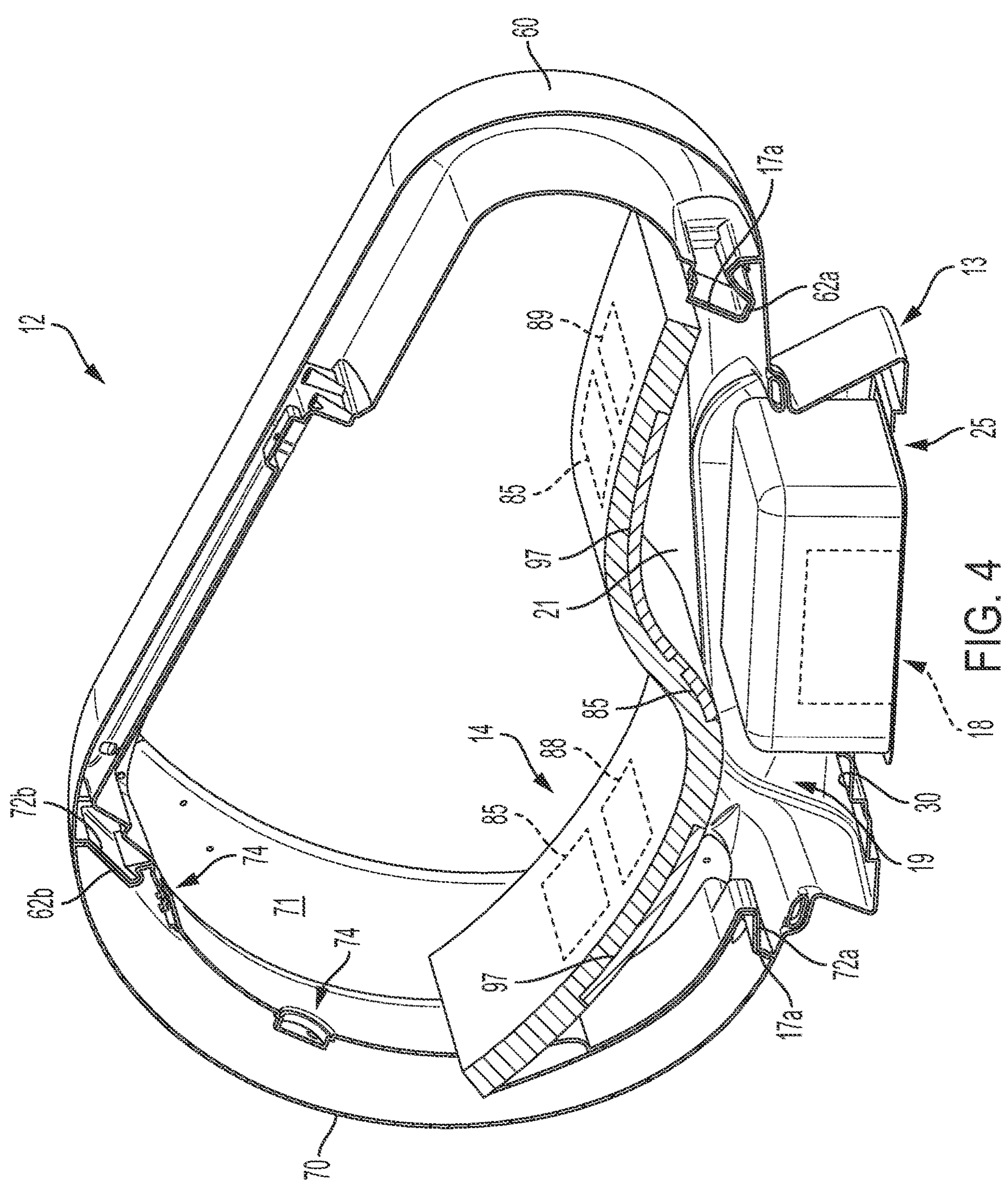
FIG. 4 is a cross-sectional view of the recovery and wellness pod apparatus shown in FIG. 2, taken along line 4-4.

Referring additionally to FIG. 4, the base housing shell 13 is preferably generally in the form of a tank or tub of an elongated configuration having a bottom wall 30 and side walls 21, and substantially open at its top to define an upwardly-facing elongated opening. Preferably, the bottom wall 30 may also define an aperture therein that is configured to receive an enclosure 25 therein for containing various components of the fluid supply arrangement 18, such as the pump 28, fluid reservoir 29, etc. As shown in FIG. 4, the perimeter of the aperture defined in the bottom wall 30 of the base housing shell 13 forms a leak-proof seal with the outer surface of the enclosure 25. As such, water utilized by the fluid spray assembly 16 during massage treatment of the user 100 is retained within the base housing shell 13 until returned to the water storage reservoir 29 within the enclosure 25 via associated piping. The base housing shell 13 may be fabricated of any suitable watertight, rigid material of appropriate strength which may be formed to the desired configuration herein described, e.g., fiberglass, plastic, or a like material. The base housing shell 13 provides an open volume 19 (FIG. 4) beneath the user support surface 34 for enclosure of various operating components of the pod apparatus 10.

As best seen in FIGS. 1A and 1B, the lateral side walls 21 of the base housing shell 13 are contoured to form a substantially planar seat back portion 22 and a seat portion 24 having a substantially-planar leg portion 29, supporting the user support surface 34. Preferably, the seat back portion 22 and the leg portion 29 are angularly oriented with respect to each other, with the seat portion 24 being disposed therebetween. The user support surface 34 is configured so that the upper and lower body portions 101 and 103, respectively, of the user 100 are supported in a generally reclining seated disposition comparable to that of a lounge-style chair wherein the user's body rests bent at the waist and knees with the upper body portion 101 partially reclined on the seat back portion 22, the upper leg extent of the lower body portion 103 slightly inclined on the seat portion 24, and the lower leg extent of the lower body portion 103 slightly declined on the leg portion. The slight bend of the knees of the user's legs help to maintain the user 100 in the proper position on the user support surface 34. As such, the pressurized water jets will impact the user 100 in the proper areas of the user's body to achieve the desired massaging effect.

A liquid medium is preferred as the fluid medium utilized by the pod apparatus 10 for supply to and emission from the fluid spray assembly 16 to produce a massage effect as hereinafter described, water being an optimal liquid in view of its ready availability and generally non-corrosive and non-caustic character. As noted, a suitable supply of water is stored in the water storage reservoir 29 for continuous circulation through the fluid supply arrangement 18 to the fluid spray assembly 16. The bottom drainage wall 30 (FIG. 2), as well as the other interior surfaces of the base housing shell 13 are configured to drain the liquid emitted from the fluid spray assembly 16 into the water storage reservoir 29. Of course, as those persons skilled in the art will readily recognize, pressurized air, other gases, and other fluidic materials could also be utilized as the fluid massaging medium without departing from the scope and substance of the present disclosure and, accordingly, the present disclosure is not intended to be and should not be construed as limited to the use of water or another liquid massage medium.

It is also preferred that the water or other massage liquid be heated to enhance the massaging effect produced by the liquid, e.g., to a temperature approximating normal body temperature, preferably in the range of 95 to 100 degrees Fahrenheit, although the apparatus has the capability of a broad range of liquid temperatures. For this purpose, a heater element (not shown) may be provided, e.g., mounted within the storage reservoir 29 below the normal level of massage liquid therein to be substantially continuously submerged in the stored massage liquid. A thermostat (not shown) is preferably provided in the electrical circuit to the heating element to provide selective control of the temperature of the massage liquid by the user.

In the preferred embodiment of the pod apparatus 10, in which the fluid spray assembly 16 is utilized for fluid massage, the user support surface 34 may be formed of a relatively thin sheet of a waterproof material affixed in watertight relationship with a flange 32 bordering the upwardly facing opening, as shown in FIG. 1. Preferably, the sheet is sufficiently thin that the impact of fluid emitted from the fluid spray assembly 16 against the underside of the sheet transmits a massaging effect through the sheet to the body of the user 100. Further, the sheet is preferably of a sufficient flexibility and resiliency to substantially conform to the body of the user 100 for maximum transmission of the massage effect through the sheet to the user 100. In this manner, the sheet functions in the nature of a waterproof membrane to keep the user 100 dry during body massage operations of the pod apparatus 10 without noticeably dampening the massaging impact of fluid emitted from the fluid spray assembly 16. For example, a latex rubber in sheet form, in the range of 15 to 55 mil. thickness, is a suitable material to provide these characteristics for the sheet, although various other commercially available rubber and plastic sheeting materials should also provide suitable results.

As a primary means of weight bearing support of the user 100, an open-mesh netting (not shown) may be affixed in tensioned condition to the flange 32 of the base housing shell 13 horizontally across its opening immediately beneath the sheet. The netting should be of sufficient strength to independently support the weight of a user 100 to provide a safety barrier in the event of a rupture or other failure of the sheet. At the same time, the open-mesh construction of the netting permits essentially unrestricted transmission of fluid from the fluid spray assembly 16 through the netting and against the underside of the sheet.

Figure 2:
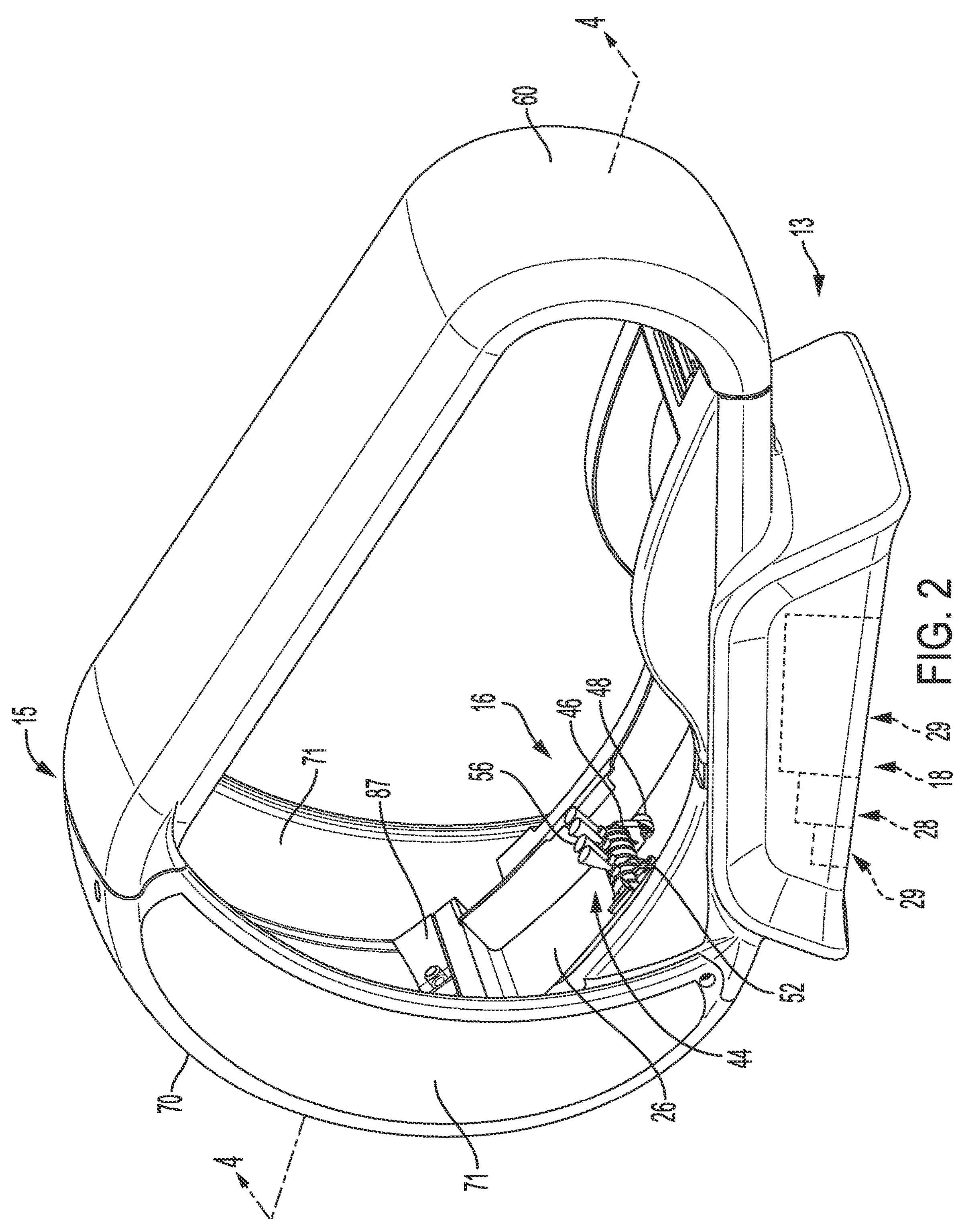
FIG. 2 is a right-side perspective view of the recovery and wellness pod apparatus shown in FIGS. 1A, 1B, and 1C, with the user support surface removed to show interior details.

Referring now to FIG. 2, the fluid spray assembly 16 includes an elongate massage spray head, generally indicated at 44, oriented transversely across substantially the widthwise extent of the user's body. The massage head 44 may be of any of various possible configurations and componentry adapted to emit the massage fluid under pressure against the underside of the sheet. For example, in one possible configuration, the massage head 44 may have a substantially hollow outer body 52 with a plurality of emission openings 56, each in the form of a nozzle, over substantially the full extent of the upward surface of the body 52 which faces the sheet. The emission openings 56 deliver pressurized fluid from the body 52 in a jet-like spray upwardly therefrom against the underside of the sheet.

The hollow outer body 52 of the massage spray head 44 is preferably formed of injection-molded upper and lower body portions. Preferably, a radiused inlet (not shown) is configured to provide a smooth inlet flow of water into the interior of the outer body 52 so that the flow within the outer body 52 is less turbulent. As well, the emission openings 56 are preferably disposed along a line that is offset from the longitudinal center axis of the hollow outer body 52. The combination of the radiused inlet 84, subsequent laminar flow within outer body 52, and the offset emission openings 56 allow the massage spray head 44 of the present pod apparatus 10 to attain an optimal massage spray that includes both laminar and turbulent flows, resulting in the desired massaging effect.

Still referring to FIG. 4, the elongated massage head 44 is supported at each opposite end by brackets 46 with rollers or wheels 48 for rolling travel along a track 26 traversingly back-and-forth through substantially the full lengthwise extent of the base housing shell 13 along angularly changing paths of travel following the angular configuration of the track 26. The angular track 26 is affixed interiorly to the bottom wall 30 of the base housing shell 13, preferably through substantially the full lengthwise extent of the base housing shell 13. The rollers 48 travel along the track 26 during lengthwise traversing travel along the track. Preferably, the track 26 is of one-piece construction. The traversing travel of the massage head 44 is driven reciprocally back-and-forth through the lengthwise extent of the base housing shell 13 via any suitable drive mechanism. For example, a toothed timing belt (not shown) may be attached at opposite belt ends to each respective bracket 46 at the ends of the massage head 44, forming two endless drive belt loops which are trained about a series of toothed guide pulleys (not shown) rotatably mounted to the interior surfaces of the side walls 21 (FIG. 4) adjacent the track 26 at each opposite end of the base housing shell 13 and also at the location of each change of angular direction in the track 26. The pulleys at one end of the base housing shell 13 would then be secured to a common drive shaft journaled through one side wall 21 and connected exteriorly thereof to a reversible drive motor (not shown) for imparting synchronous drive motion to the belts and, in turn, to the massage head 44 to travel along the track 26.

The pressurized fluid is delivered from the fluid supply arrangement 18 to the massage head 44 in any suitable way. For example, the pressurized fluid supply arrangement 18 may have an electric motor 90 driving the liquid pump 26 to draw fluid from the liquid storage reservoir 29, both the liquid pump 26 and the water storage reservoir 29 being stored within the enclosure 25 of the base housing shell 13. The outlet side of the pump 26 delivers the fluid under pressure to the massage head 44 through a suitable conduit (not shown) that is in fluid communication with the outer body 52 of the massage head 44.

Figure 3A:
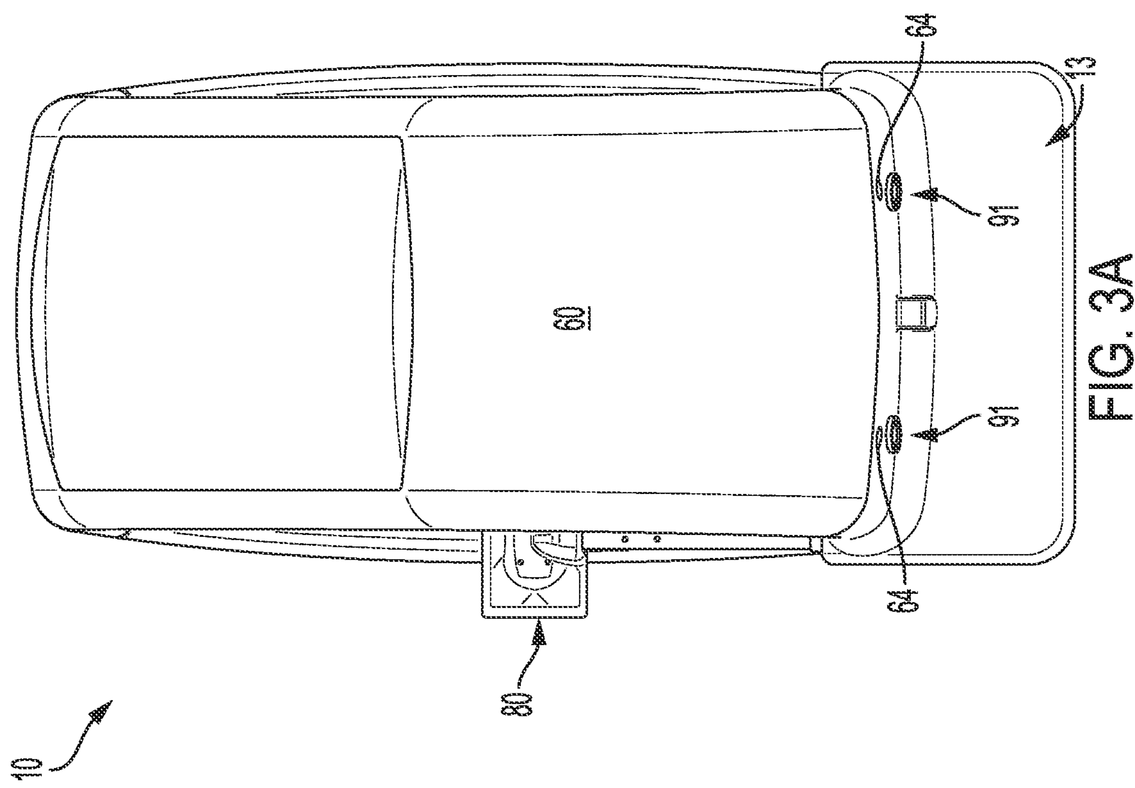
FIGS. 3A, 3B, 3C, and 3D are front, rear, top, and bottom plan views of the recovery and wellness pod apparatus shown in FIGS. 1A, 1B, and 1C.
Figure 3B:
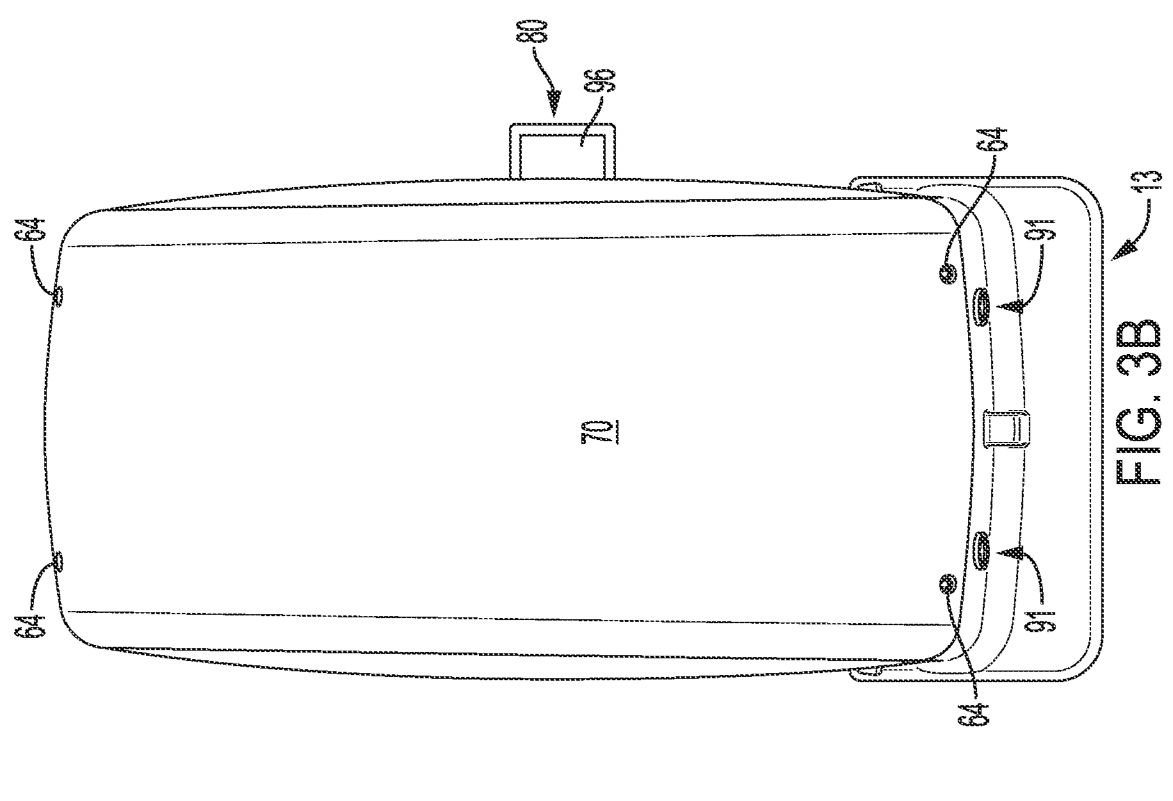
Figure 3C:
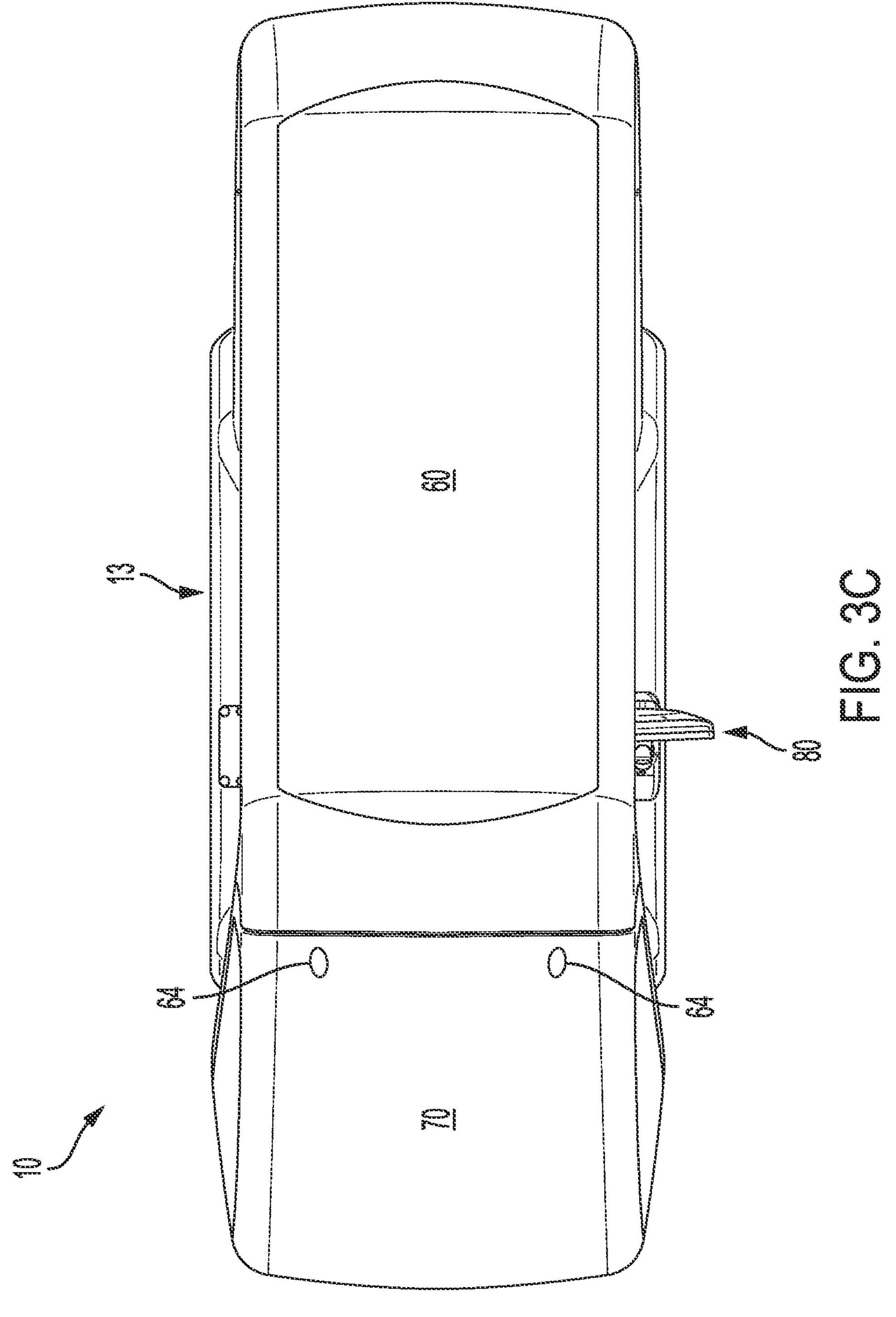
Figure 3D:
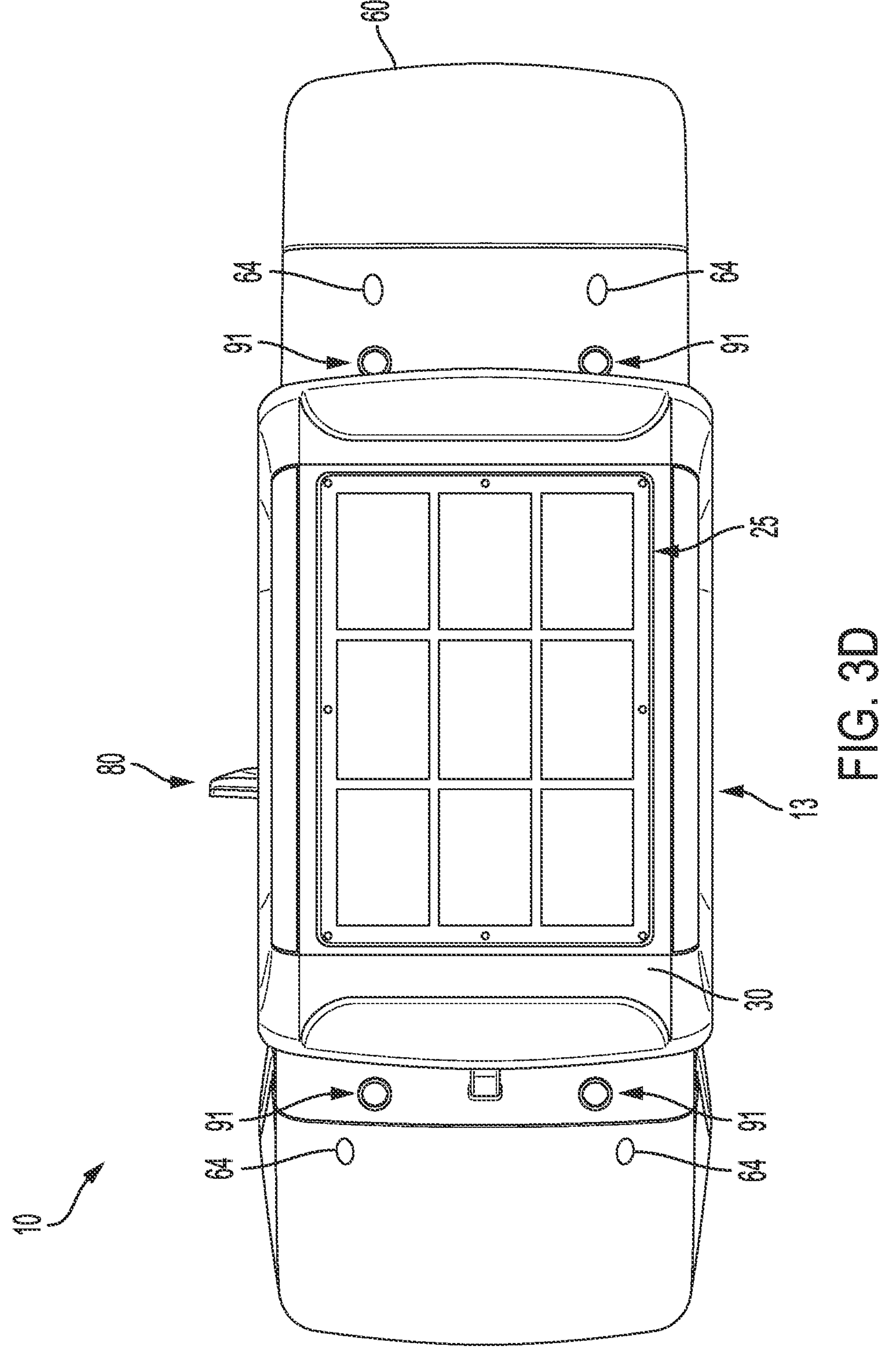

Referring now to FIGS. 1A and 4, the pod apparatus 10 includes a top cover structure 15 that is preferably constructed of a hollow front cover shell 60 and a hollow rear cover shell 70. Similarly to the base housing shell 13, front cover shell 60 and rear cover shell 70 are preferably formed by a rotomolding operation, with the front cover shell 60 including a pair of opposed flanges 62*a*/62*b* and the rear cover shell 70 including a pair of opposed flanges 72*a*/72*b*. As best seen in FIG. 4, a first flange 72*a* of rear cover shell 70 is correspondingly shaped to a first flange 17*a* of the base housing shell 13. Similarly, a first flange 62*a* of the front cover shell 60 is correspondingly shaped to a second flange 17*b* of the base housing shell 13. Once the correspondingly-shaped flanges are matingly positioned adjacent each other, a plurality of fasteners 64 are utilized to secure the front cover shell 60 and the rear cover shell 70 to the base housing shell 13, as best seen in FIG. 3D. Additionally, front cover shell 60 includes a second flange 62*b* that is correspondingly-shaped to the second flange 72*b* of the rear cover shell 70. As shown in FIG. 3C, fasteners 64 are also used to secure the adjacent flanges of the front cover shell 60 and the rear cover shell 70 together. By forming the housing structure 12 of hollow rotomolded portions, assembly of the pod apparatus 10 is simplified as all wiring, liquid piping, electrical components, etc., may be readily routed and disposed within the hollow housing structure 12. Note also, the front cover shell 60 includes a recess 66 for receiving a video display panel 86, whereas the rear cover shell 70 includes a pair of recesses 74 for receiving either fans, or vents, of a climate control system, as discussed in greater detail below. Note, in alternate embodiments, the housing structure 12 may be formed of more than, or less than, three shell portions. Moreover, the housing structure need not be formed by rotomolding in alternate embodiments.

Still referring to FIGS. 1A and 4, the preferred embodiment of the housing structure 12 of the pod assembly 10 also includes a pair of side panels 71 extending forwardly from the rear cover portion 70 in the vicinity of the head of the user 100. The side panels 71, along with the top cover portion 15, offer the user a feeling of privacy not afforded by standard massage beds. However, because the remainder of each side of the pod assembly remains open, a user 100 should be able to get the feeling of privacy while avoiding any feelings of claustrophobia. However, in alternate embodiments, one side of the pod assembly may be fully enclosed while the opposite side remains open. Further, in alternate embodiments, a curtain or shade may be provided on the open side, or sides, for full privacy when desired. Although the embodiment shown is designed to support only one user, alternate embodiments may be wide enough so that multiple users may utilize the pod assembly simultaneously.

Referring again to FIG. 4, an alternate embodiment of a pod apparatus is discussed. Although the housing structure 12 is practically identical to that of the previously discussed embodiment (FIGS. 1A, 1B, and 1C), the present embodiment does not include a fluid spray assembly 16. Rather, the present embodiment includes one or more of heating elements 85, vibratory motors, or liquid bags 97 disposed within the user support surface 14. The user support surface 14 is substantially thicker than that of the first embodiment so that the components noted above may be stored therein in close contact to the user. Where liquid bags 97 are present, a fluid supply arrangement 18 is required to circulate liquid of the desired temperature through the liquid bags 97. However, in these embodiments where only heating elements 85 and vibratory motors 87 are utilized, the fluid supply may be omitted, as well as the enclosure 25.

Figure 5:
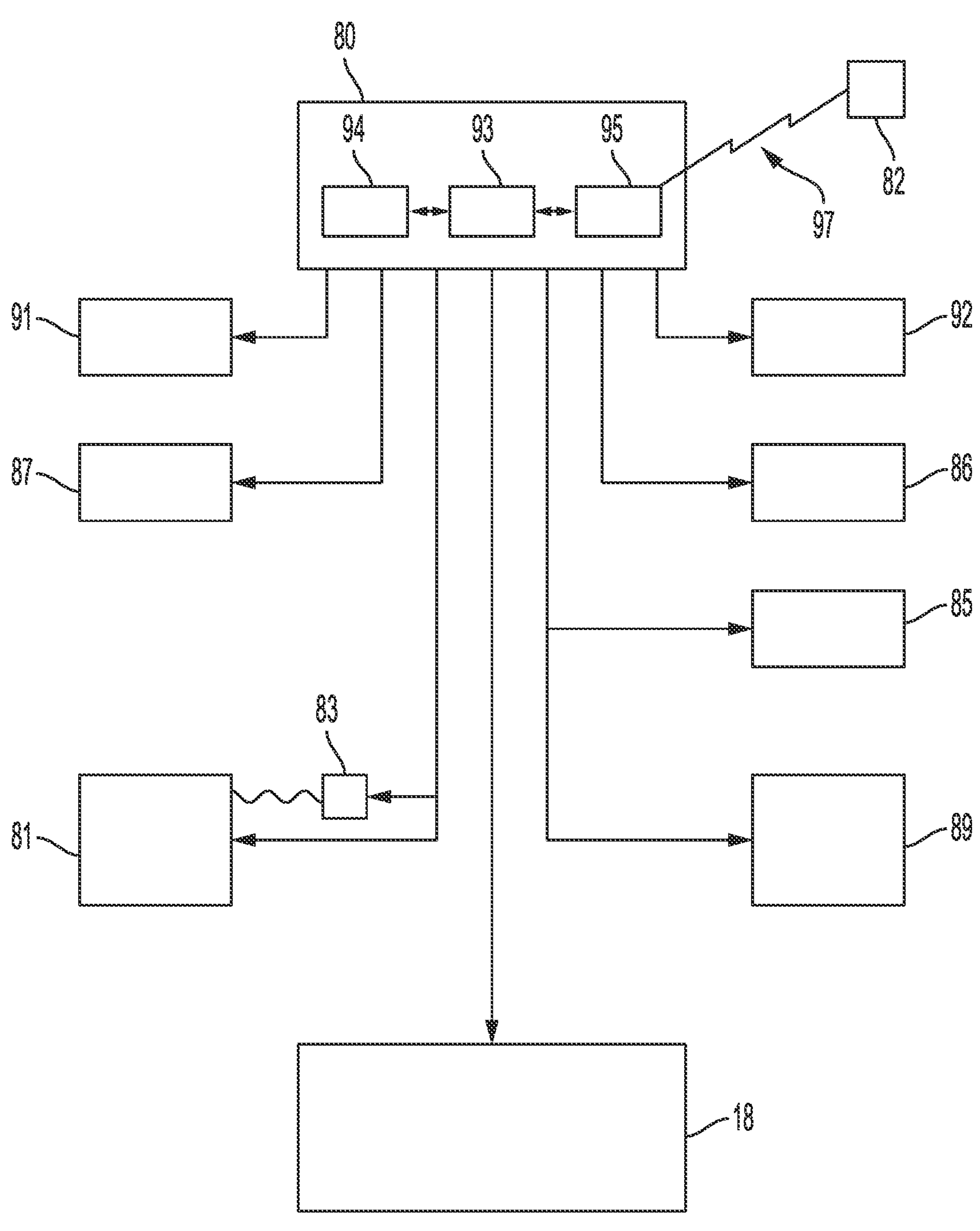
FIG. 5 is a block diagram of an example recovery and wellness pod apparatus architecture in accordance with the sample embodiments.
Figure 6:
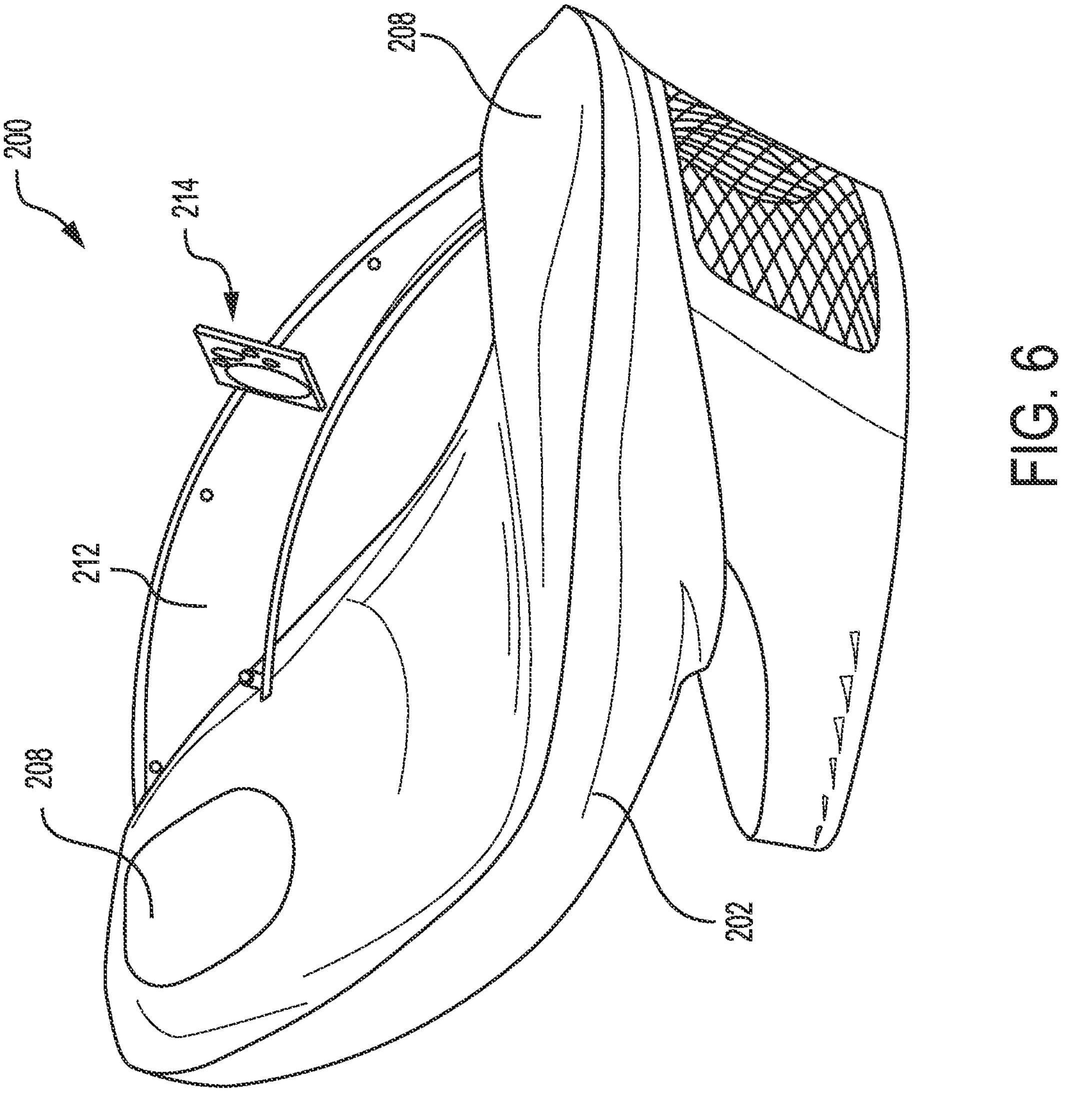
FIG. 6 is a perspective of a cold and heat therapy apparatus in accordance with an alternate embodiment of the present disclosure.
Figures 7A, 7B:
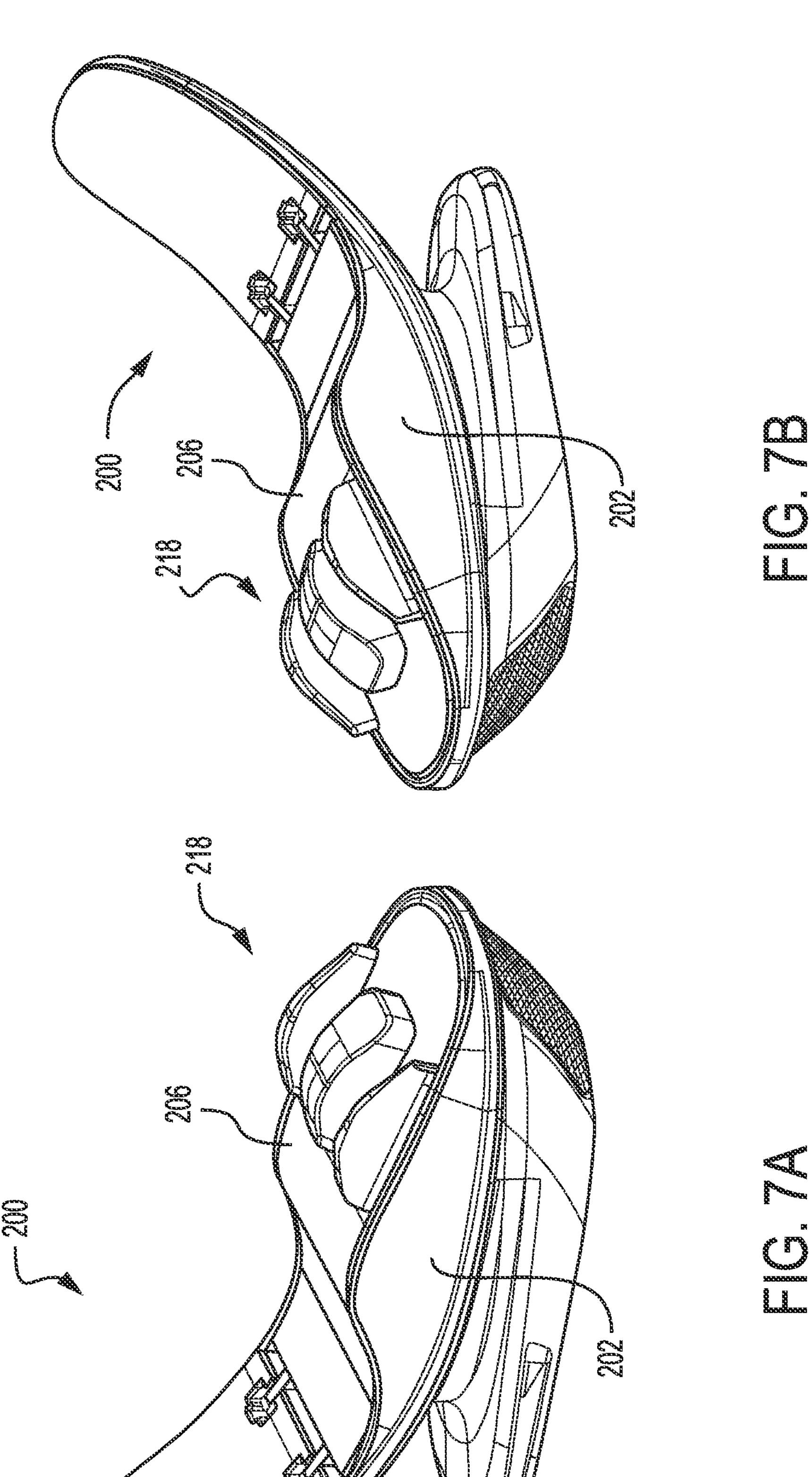
FIGS. 7A and 7B are right side and left side perspective views of an alternate embodiment of a cold and heat therapy apparatus in accordance with an alternate embodiment of the present disclosure.
Figure 8B:
FIGS. 8A and 8B are left and right side views of the cold and heat therapy apparatus shown in FIGS. 7A and 7B.
Figure 8B:
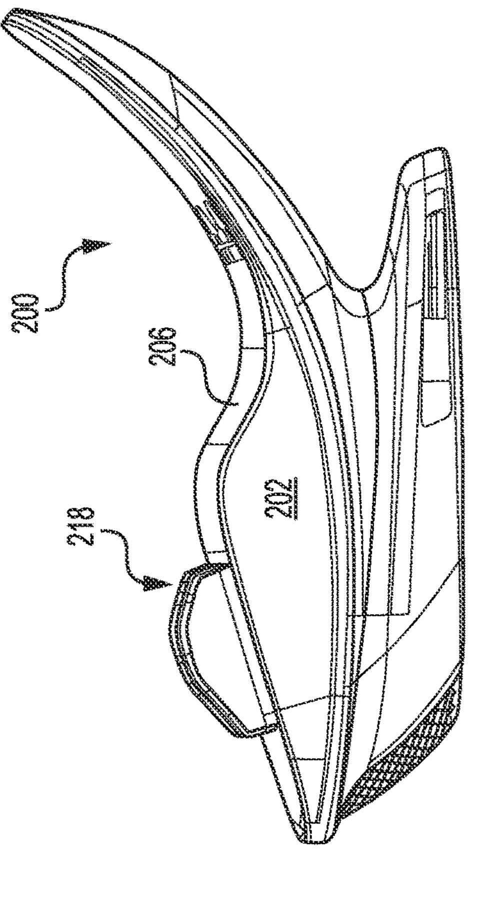
Figure 8A:
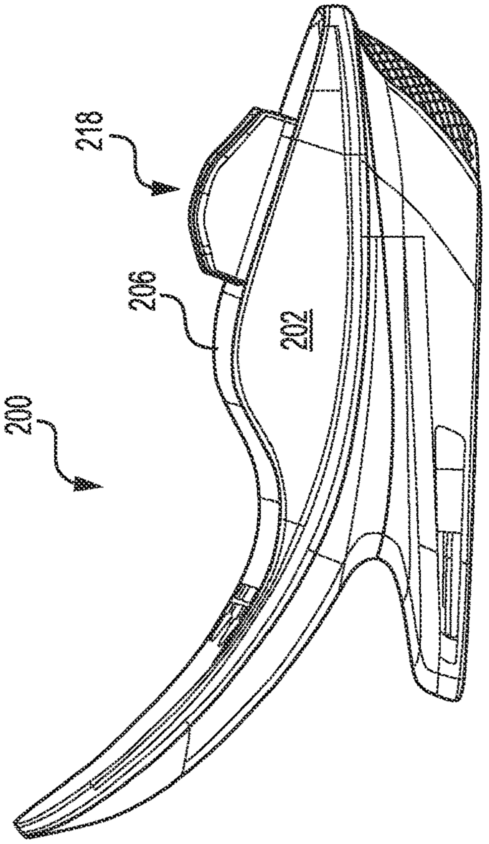
Figures 9A, 9B:
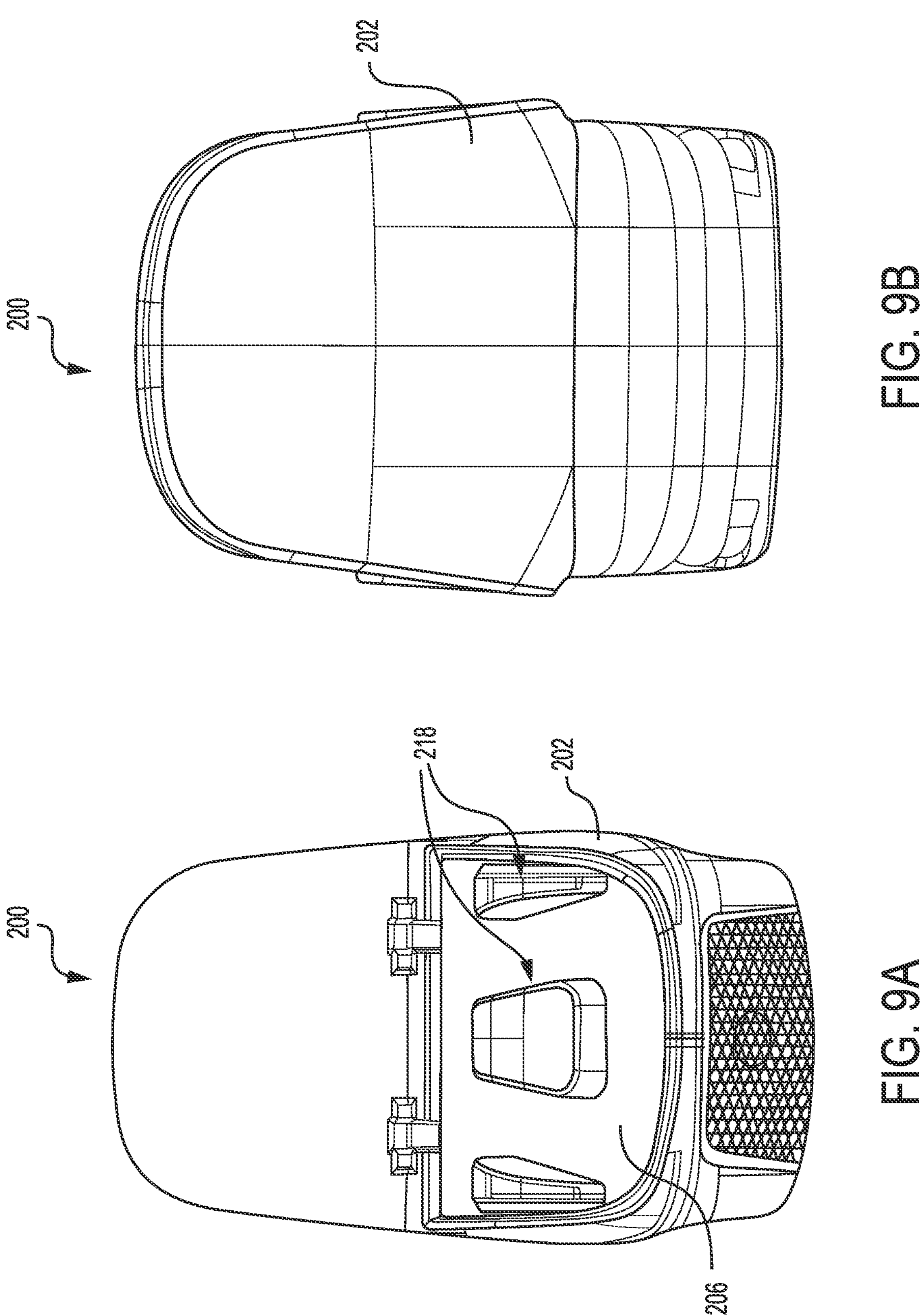
FIGS. 9A and 9B are front and back views of the cold and heat therapy apparatus shown in FIGS. 7A and 7B.
Figure 10B:
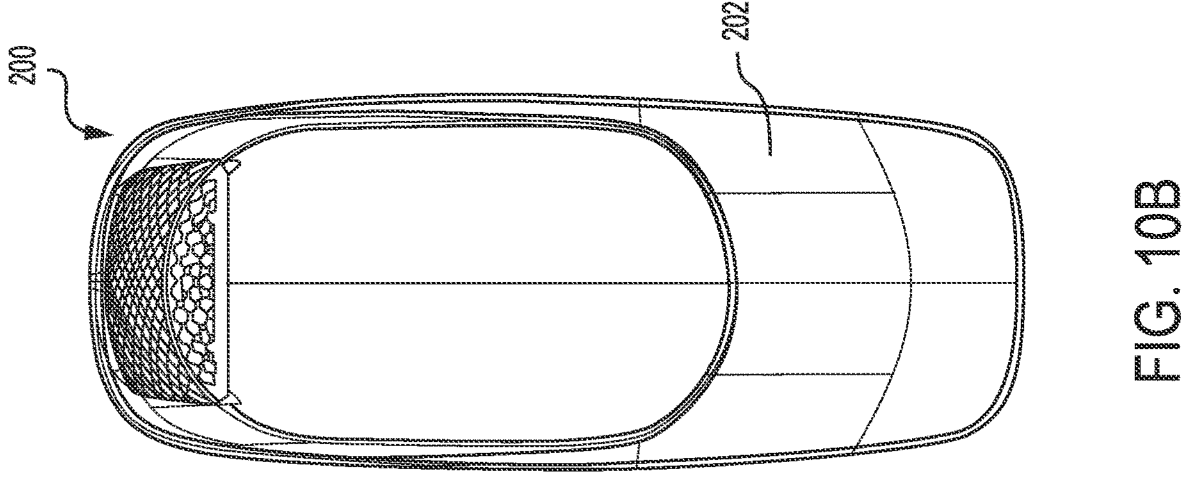
FIGS. 10A and 10B are top and bottom views of the cold and heat therapy apparatus shown in FIGS. 7A and 7B.
Figure 10A:
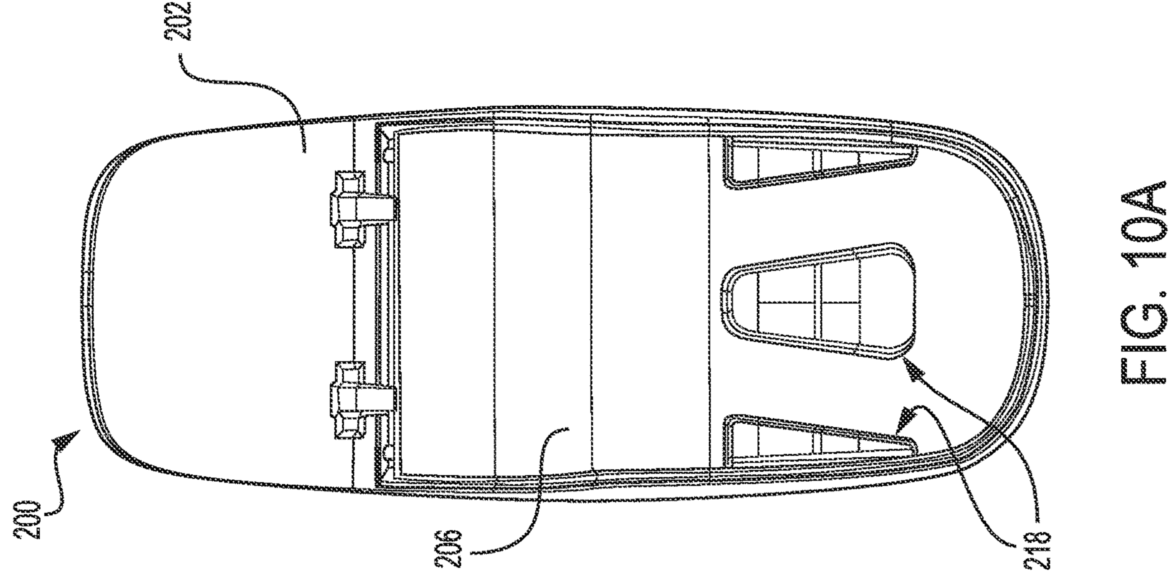

Referring now to FIG. 5, the recovery and wellness pod apparatus 10 is configured to perform a number of therapeutic operations on a user 100. For example, not only does the pod apparatus 10 include an ergonomic user support surface 14 to properly position the user during operations such as, but not limited to, hydrotherapy, vibratory massage, and heat treatments, as discussed in greater detail below, but the pod apparatus 10 also includes a large video display panel 86 received in recess 66 of the front cover shell 60, audio speakers 87 mounted to the inner wall of the front cover shell 60 (as shown in FIG. 2) adjacent the user's head, fans or vents 81 received in recesses 74 of the rear cover portion 70, a scent chamber 83 associated with the fans/vents of the climate control system, heating and/or vibrating motors 85 and 89 (FIG. 4), respectively, disposed within the user support surface 14, and as previously discussed, the fluid supply arrangement 18 for performing water massage treatments. All of these operations may be controlled by a user interface display 80 that is positioned for easy access by a user 100 while disposed on the user support surface 34, as best seen in FIG. 1A. For example, by way of a touchscreen 96 on the user interface display 80, the user 100 may select content for display on the video display panel 86 that may include, but is not limited to, nature relaxation videos, guided meditation videos, travel videos, healthy living videos, reading exercise videos, motivational/inspirational videos, and mindfulness videos. The audio to accompany these videos or wellness content is preferably provided by the speakers 87. Note, however, if the video display panel 86 is not being utilized, the speakers 87 may be utilized to listen to alternate content such as music, podcasts, etc. The speakers 87 are positioned adjacent the user's head so that the user 100 can enjoy full audio, yet not disturb others in the surrounding environment. Note also, the video display panel 86 may be utilized for viewing movies, standard programming, playing video games, etc.

In a preferred embodiment of the pod apparatus 10, the vents 81 of a climate control system are disposed within the pod apparatus 10 so that a user 100 may select to create air flow that is either warmer or cooler than the surrounding environment. Alternately, fans may be used in place of a climate control system so that ambient air is merely recirculated. Working in concert with the climate control system, a scent chamber 83 is provided that when activated by the user 100, releases a desired scent that will pass through the vents 81 (or fans) of the climate control system. For example, a scent option may be selected that accompanies a video experience that a user 100 is viewing on the video display panel, such as a pine scent when viewing a program related to forests. Users may also activate heating elements 85 and/or vibratory motors 89 (FIG. 4) that are disposed within the user support surface 14 to provide a vibration massage and/or heat treatment. Alternately, as discussed in greater detail above with regard to preferred embodiments that include hydrotherapy operations, the user 100 may control the fluid supply arrangement 18 to select the appropriate level of massage and desired temperature of the liquid being utilized.

Additionally, as best seen in FIG. 3D, the user interface display 80 may be used to control LED lighting 91 that is disposed on the underside of the housing structure 12 for the purpose of adding a slight illumination to the room in which the pod apparatus 10 is located. As well, any of a plurality of sensors 92 including, but not limited to, respiratory sensors, pulse oximeters, heart rate monitors, eye motion sensors, etc., may be controlled and monitored through the user interface display 80.

As shown in FIG. 5, the user interface display may include a process 93, a memory 94, and a communications interface 95. The processor 93 may be any means configured to execute various programmed operations or instructions stored in a memory device such as a device or circuitry operating in accordance with software or otherwise embodied in hardware or a combination of hardware and software thereby configuring the device or circuitry to perform the corresponding functions of the processor 93 as described herein. In this regard, the processor 93 may be configured to analyze electrical signals communicated thereto in the form of user input commands via the touchscreen. The memory 310 may be configured to store instructions, computer program code, programming, health information, etc., in a non-transitory computer-readable medium for use, such as by the processor 305. The communication interface 95 may be configured to enable connection to external systems. In this manner, the processor 93 may retrieve stored data from external servers via the communication interface 95, in addition to or as an alternative to the memory 94. For example, a user may input commands through a wireless connection 111 with the communications interference 95 with a personal electronic device 82 such as, but not limited to, a cell phone, tablet, laptop computer, etc.

Figures 11, 12:
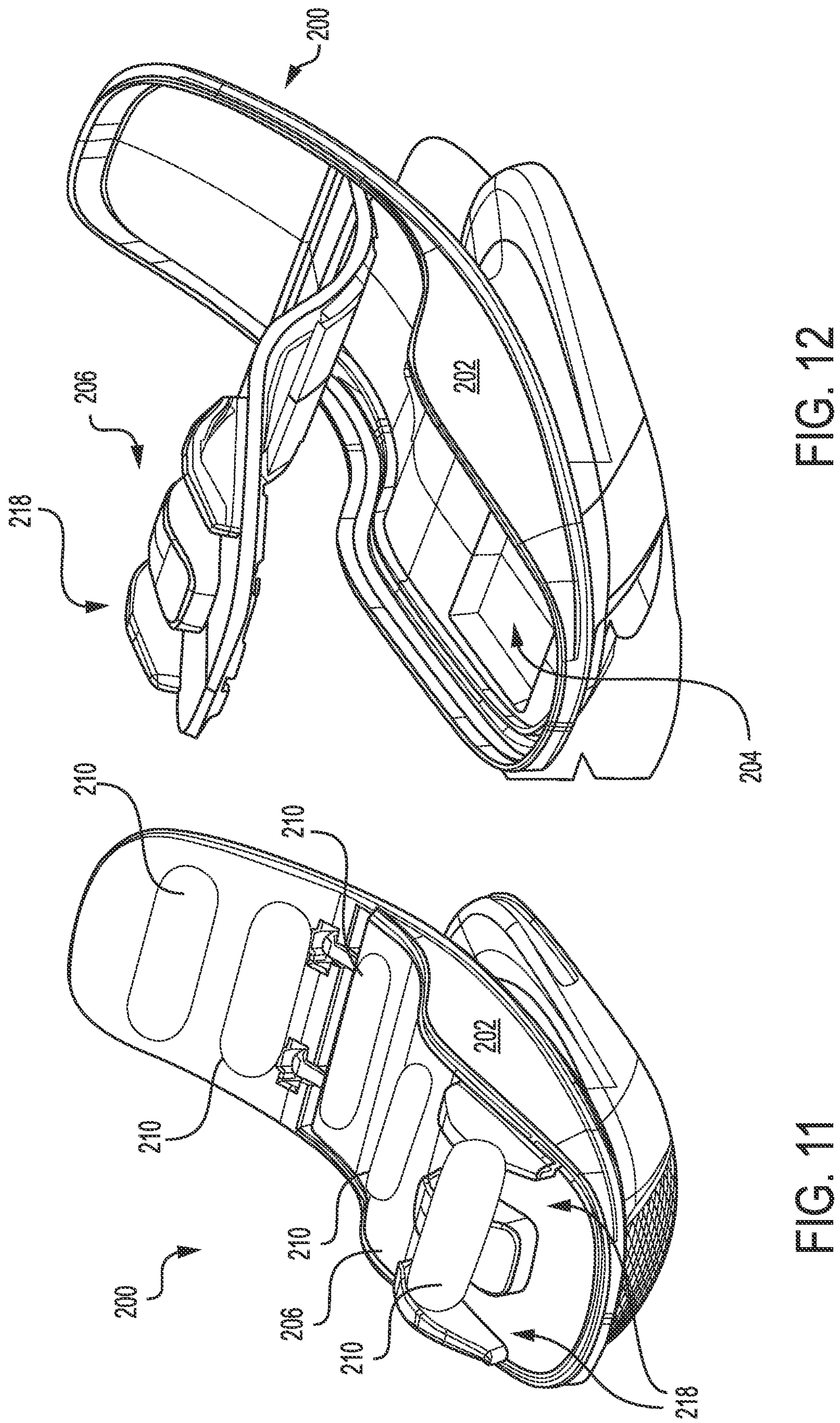
FIG. 11 is a perspective view of the cold and heat therapy apparatus shown in FIGS. 7A and 7B, showing a preferred location of various liquid bags disposed within the user support surface.
FIG. 12 is a perspective view of the cold and heat therapy apparatus shown in FIGS. 7A and 7B, with the seating surface lid in the open position.
Figure 13A:
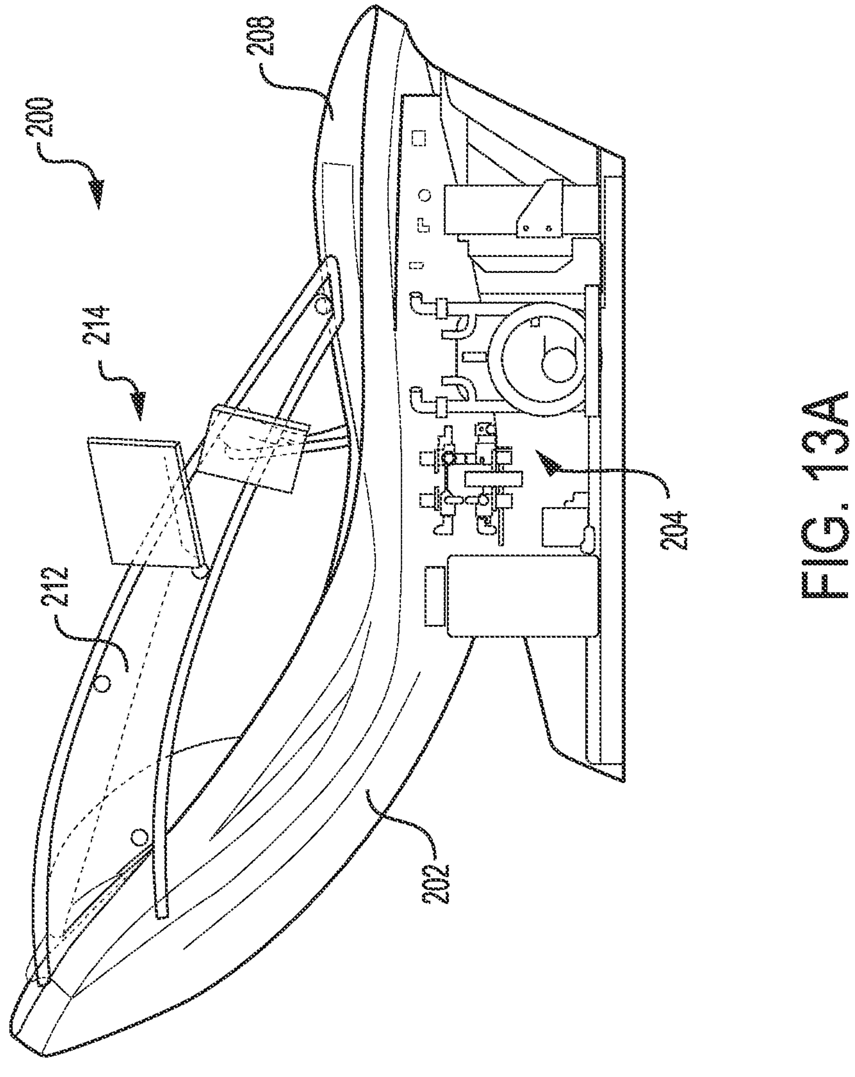
FIGS. 13A and 13B are cross-sectional side and perspective views of the cold and heat therapy apparatus shown in FIGS. 7A and 7B.
Figure 13B:
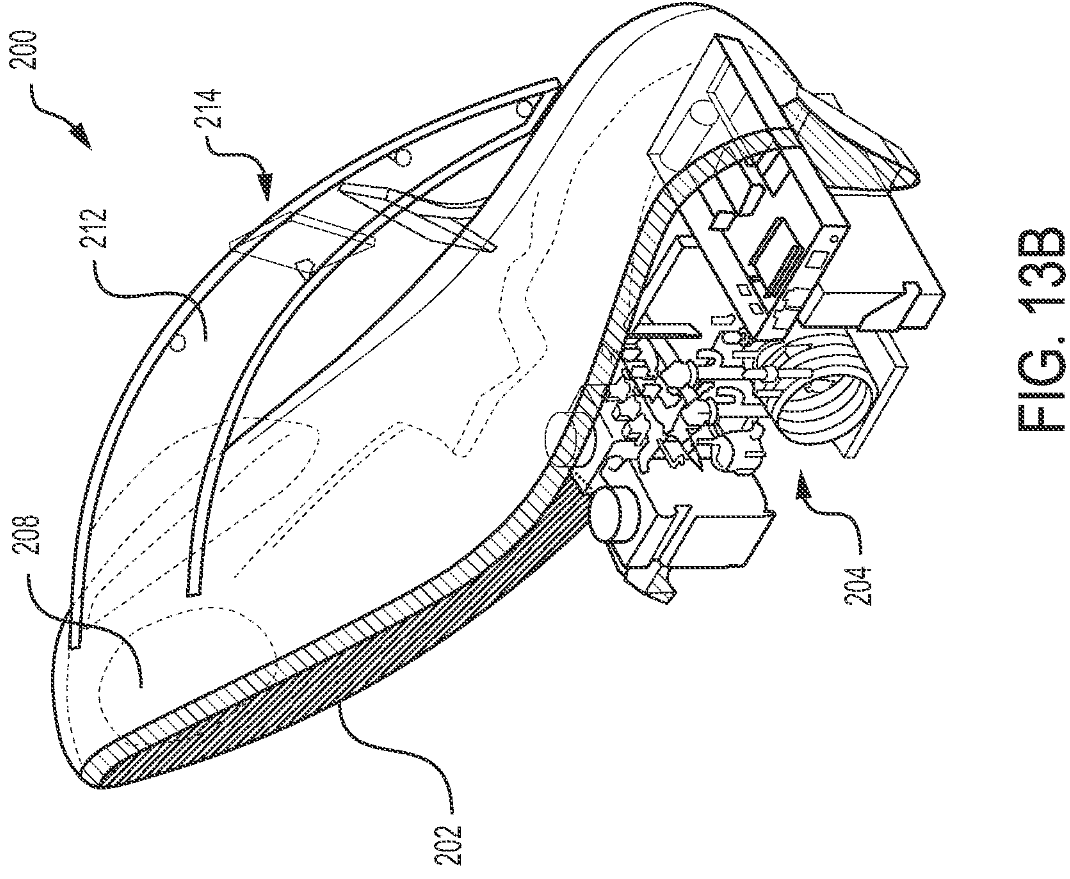

Referring now to FIGS. 6 through 12, an embodiment of an apparatus for cold and heat therapy of a user in a reclined position is shown. As shown, the therapy apparatus 200 includes a molded composite body 202 that defines an internal cavity 204 for housing the various components of the apparatus, as best seen in FIGS. 13A and 13B. A molded composite seat pan lid 206, as best seen in FIG. 12, forms part of the user support surface 208 of the therapy apparatus 200 and allows access to the interior cavity 204 thereof for access and maintenance of the various components. For example, solenoids and a manifold are utilized to adjust the direction and flow of the appropriate temperature water, either hot or cold, to the desired area of the body by causing flow to and from the appropriate liquid bags 210. As best seen in FIG. 11, multiple liquid bags 210 are disposed in the user support surface of the therapy apparatus 200 to allow the user to select the portion of their body to which the hot and/or cold temperatures will be applied. Two evaporators operate in conjunction with a compressor to remove cold and heat from the compressor and direct the desired temperature water to the manifold. The flow of water is controlled by two pumps that operate in response to monitored temperatures within the system to control the flow of water. The heater and the thermostat maintain the temperature of the water when the apparatus is not in use and may also assist in increasing water temperatures quickly should the user desire to significantly increase the temperature. Similarly, a heat exchanger is utilized to remove heat from water when the user selects cooler temperatures. The liquid bags 210 are securely and safely held in molded areas near the user that are easy to access but still protect the bags 210 so they do not get damaged as a user gets on or off the apparatus.

Referring again to FIG. 6, the therapy apparatus 200 includes a privacy screen 212 that may be universally mounted to either side of the housing 202, and includes a customer electronic control board 214 having an interactive graphic user interface for controlling of the functions of the apparatus. In addition to the liquid circulatory system, the therapy apparatus 200 also includes a pneumatic pump and compression bags 218, such as for the lower extremities of the user where an air is flowed into the compression bags 218 allowing them to conform to the user's body. Preferably, the bags 218 are encapsulated within the user support surface and are ergonomic thereby conforming to the body of the user. The therapy apparatus 200 allows for compression therapy to be administered to the various regions such as, but not limited to, legs, arms, hands, feet, and the head/neck region. The user may control the variable speed pneumatic pump by way of the graphic user interface 214 to provide air palpitations/compression of varying strengths. The air bladder may also be used to aid in wrapping the cold/heat therapy liquid bags 210 closer to the body of the user, thereby improving heat transfer. Additionally, the therapy apparatus 200 provides for active monitoring of all systems to include pressure monitoring and temperature monitoring of the fluid system, flow monitoring of the fluid system, pressure monitoring of the air/vacuum compression system, and active monitoring of water levels within the system.

Figure 14:
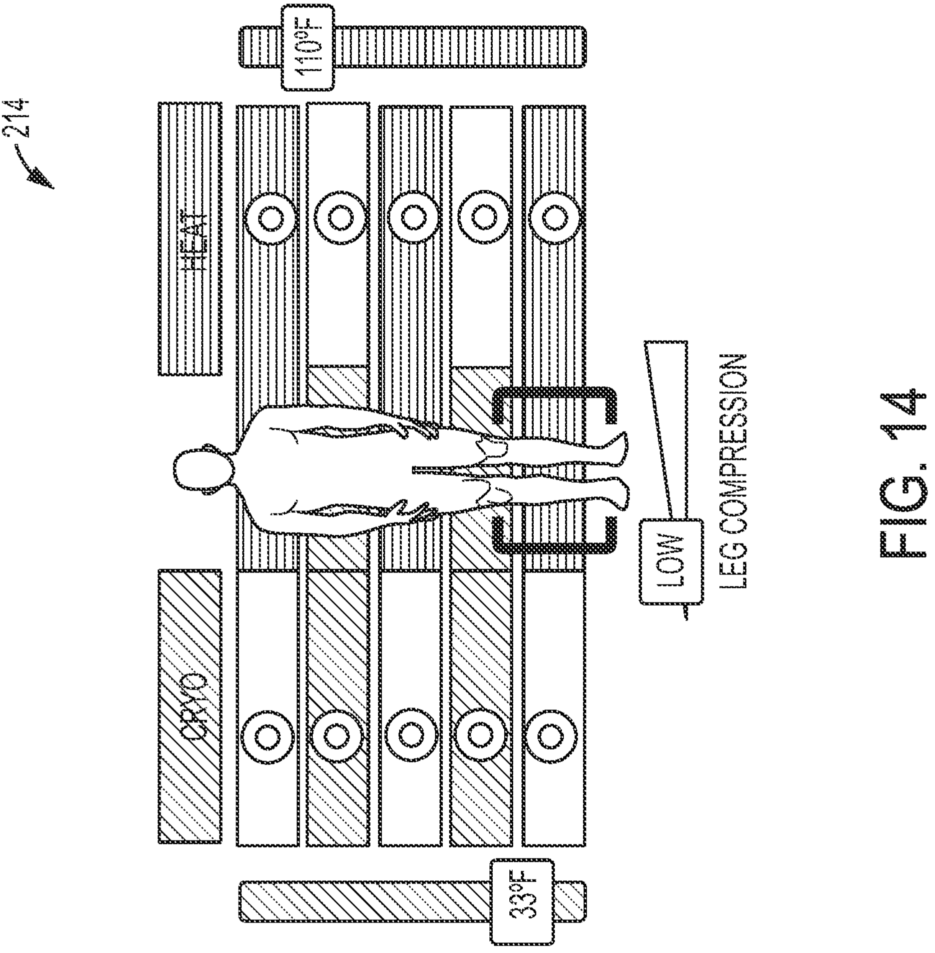
FIG. 14 is a schematic representation of application of cold and hot temperature being applied to a user.

An objective of the therapy apparatus 200 is to provide a solution to deliver cold and heat therapy in a commercial setting, by alleviating issues such as direct contact with liquid, presence of a highly trained operator, etc., that exist with known methods of cold and heat therapy. Referring specifically to FIGS. 11 and 14, an embodiment of the disclosed therapy apparatus allows a user to select from six different zones to indicate where they would like to experience cold (28° to 40° F.), or heat (90° to 120° F.), therapy to target sore muscles, back pain, etc. By offering concurrent cold and heat therapies, the user may enjoy the benefit of extreme cold therapy in targeted areas (for example, lower back and ham strings), yet apply heat to other areas of the body (for example, neck, upper back, and calves), thereby allowing the user to remain comfortable throughout the session as the heat offsets the cold. The user may also activate a contrast therapy setting to switch the hot/cold therapies, and also activate compression therapy on the various lengths. As shown in FIG. 11, compression therapy is possible for the legs. Additionally, adjustable compression cuffs (not shown) may be provided that allow the user to provide compression therapy to their arms, hands, feet, etc., as desired. Note also, an external liquid bladder (not shown) is preferably provided that allows the bladder to be positioned on the user's body independently of the user's position on the user support surface.

It will therefore be readily understood by those persons skilled in the art that the present disclosure is susceptible of a broad utility and application. Many embodiments and adaptations of the present disclosure other than those herein described, as well as many variations, modifications and equivalent arrangements, will be apparent from or reasonably suggested by the present disclosure and the foregoing description thereof, without departing from the substance or scope of the present disclosure. Accordingly, while the present disclosure has been described herein in detail in relation to its preferred embodiment, it is to be understood that this disclosure is only illustrative and exemplary of the present disclosure and is made merely for purposes of providing a full and enabling disclosure of the invention. The foregoing disclosure is not intended or to be construed to limit the present disclosure or otherwise to exclude any such other embodiments, adaptations, variations, modifications and equivalent arrangements, the present disclosure being limited only by the claims appended hereto and the equivalents thereof.

The invention claimed is:

1. An apparatus for cryotherapy treatment of a user in a reclined position, comprising:

- a housing structure having a base portion with a user support surface for supporting the user in a reclined position;
- a first liquid storage reservoir operative to hold a quantity of liquid at a first temperature;
- a second liquid storage reservoir operative to hold a quantity of the liquid at a second temperature greater than the first temperature;
- a plurality of liquid bags at the user support surface, the liquid bags being in selective fluid communication with the first liquid storage reservoir and the second liquid storage reservoir so that the liquid bags are each individually and alternatively fillable with liquid of the first temperature and liquid of the second temperature such that at least one of the liquid bags will contain liquid of the first temperature and at least one other of the liquid bags will simultaneously contain liquid of the second temperature.

2. The apparatus of claim 1, wherein the first temperature is from 28° F. to 40° F.

3. The apparatus of claim 2, wherein the second temperature is from 90° F. and 120° F.

4. The apparatus of claim 3, further comprising a plurality of compression bags that are inflated by air.

5. The apparatus of claim 4, wherein the compression bags are located to provide compression to the legs of the user.

6. The apparatus of claim 1, wherein the plurality of liquid bags comprise first, second, third, fourth, and fifth liquid bags that are respectively positioned to be adjacent a neck, upper back, lower back, hamstrings, and calves of the user when the user is on the user support surface in the reclined position.

7. The apparatus of claim 1, further comprising a plurality of solenoids operative to adjust the direction and flow of the liquid of the first temperature and the liquid of the second temperature to selected ones of the plurality of liquid bags.

8. The apparatus of claim 7, further comprising a single compressor is utilized to produce the liquid of the first temperature and the liquid of the second temperature.

9. The apparatus of claim 8, wherein the single compressor operates in conjunction with two evaporators.

10. The apparatus of claim 8, further comprising a heater that assists in increasing liquid temperature.

11. The apparatus of claim 1, wherein the user support surface further comprises a substantially planar seat back portion, a substantially planar leg portion, and a seat portion disposed therebetween, wherein the seat back portion and the leg portion form an angle therebetween.

12. The apparatus of claim 1, wherein the plurality of liquid bags are held in molded areas of the housing structure.

13. An apparatus for cryotherapy treatment of a user in a reclined position, comprising:

- a housing structure having a base portion with a user support surface for supporting the user in a reclined position;
- a first liquid storage reservoir operative to hold a quantity of liquid at a first temperature of from 28° F. to 40° F.;
- a second liquid storage reservoir operative to hold a quantity of the liquid at a second temperature of from 90° F. and 120° F.;
- a first liquid pump in fluid communication with the first liquid storage reservoir;
- a second liquid pump in fluid communication with the second liquid storage reservoir;
- first, second, third, fourth, and fifth liquid bags in selective fluid communication with the first liquid storage reservoir and the second liquid storage reservoir so that the liquid bags are each individually and alternatively fillable by one of the first liquid pump and the second liquid pump with liquid of the first temperature and liquid of the second temperature such that at least one of the liquid bags will contain liquid of the first temperature and at least one other of the liquid bags will simultaneously contain liquid of the second temperature; and
- the plurality of liquid bags being respectively positioned to be adjacent a neck, upper back, lower back, hamstrings, and calves of the user when the user is on the user support surface in the reclined position.

14. The apparatus of claim 13, further comprising a plurality of solenoids operative to adjust the direction and flow of the liquid of the first temperature and the liquid of the second temperature to selected ones of the plurality of liquid bags.

15. The apparatus of claim 14, further comprising a single compressor is utilized to produce the liquid of the first temperature and the liquid of the second temperature.

16. The apparatus of claim 15, wherein the single compressor operates in conjunction with two evaporators.

17. The apparatus of claim 15, further comprising a heater that assists in increasing liquid temperature.

18. The apparatus of claim 13, wherein the liquid comprises water.

19. The apparatus of claim 13, further comprising a plurality of compression bags that are inflated by air.

20. The apparatus of claim 19, wherein the compression bags are located to provide compression to legs of the user.

* * * * *